(12) United States Patent
Pieken et al.

(10) Patent No.: US 7,098,326 B2
(45) Date of Patent: Aug. 29, 2006

(54) METHODS FOR THE INTEGRATED SYNTHESIS AND PURIFICATION OF OLIGONUCLEOTIDES

(75) Inventors: Wolfgang Pieken, Boulder, CO (US); Andreas Wolter, Hamburg (DE); Michael Leuck, Boulder, CO (US)

(73) Assignee: Sigma-Aldrich Co., St. Louis, MO (US)

( * ) Notice: Subject to any disclaimer, the term of this patent is extended or adjusted under 35 U.S.C. 154(b) by 155 days.

(21) Appl. No.: 10/349,195

(22) Filed: Jan. 22, 2003

(65) Prior Publication Data

US 2003/0195351 A1 Oct. 16, 2003

Related U.S. Application Data

(60) Provisional application No. 60/351,991, filed on Jan. 23, 2002.

(51) Int. Cl.
*C07H 21/00* (2006.01)
*C07H 21/02* (2006.01)
*C07H 21/04* (2006.01)

(52) U.S. Cl. .................. 536/25.3; 536/25.34

(58) Field of Classification Search ............. 536/25.3, 536/25.34

See application file for complete search history.

(56) References Cited

U.S. PATENT DOCUMENTS

| | | | |
|---|---|---|---|
| 4,291,024 A | 9/1981 | Turcotte | |
| 4,349,552 A * | 9/1982 | Takaya et al. ............. | 514/274 |
| 4,415,732 A | 11/1983 | Caruthers et al. | |
| 4,458,066 A | 7/1984 | Caruthers et al. | |
| 4,616,071 A | 10/1986 | Holubka | |
| 4,725,677 A | 2/1988 | Köster et al. | |
| 5,049,656 A | 9/1991 | Lewis et al. | |
| 5,093,232 A | 3/1992 | Urdea | |
| 5,118,800 A | 6/1992 | Smith et al. | |
| 5,118,802 A | 6/1992 | Smith et al. | |
| 5,200,514 A | 4/1993 | Chu | |

(Continued)

FOREIGN PATENT DOCUMENTS

DE 25 31 257 1/1976

(Continued)

OTHER PUBLICATIONS

U.S. Appl. No. 09/845,742, filed May 1, 2001, Pieken et al.

(Continued)

*Primary Examiner*—Jezia Riley
(74) *Attorney, Agent, or Firm*—Sigma-Aldrich Corp.; Brian Stiernalt; Jeffrey Wilson

(57) ABSTRACT

The present invention discloses novel methods for the integrated synthesis and purification of oligonucleotides. The methods employ novel capping reagents carrying two functional groups. The first functional group provides for a smooth and efficient capping process and incorporates the second functional group into contaminant oligonucleotides during solid phase oligonucleotide synthesis. The second functional group functions as a chemical purification handle in the trapping of truncated oligonucleotides (failure sequences) on a solid support. The trapping process creates covalent bonds between the solid support and the truncated oligonucleotides and therefore allows the removal of the truncated sequences from the desired full length oligonucleotide product by filtration. The chemical trapping process employed in this invention is based on cycloaddition reactions, particularly Diels-Alder reactions between the truncated oligonucleotides and the trapping agent. The invention includes novel solid support compositions that carry covalently attached Diels-Alder reaction components.

22 Claims, 6 Drawing Sheets

U.S. PATENT DOCUMENTS

| | | | |
|---|---|---|---|
| 5,221,736 | A | 6/1993 | Coolidge et al. |
| 5,393,877 | A | 2/1995 | McLean et al. |
| 5,420,276 | A | 5/1995 | Norbeck |
| 5,464,759 | A | 11/1995 | Coolidge et al. |
| 5,466,786 | A | 11/1995 | Buhr |
| 5,539,082 | A | 7/1996 | Nielsen et al. |
| 5,552,535 | A | 9/1996 | McLean et al. |
| 5,576,429 | A | 11/1996 | Johansson |
| 5,580,697 | A | 12/1996 | Keana et al. |
| 5,874,532 | A | 2/1999 | Pieken et al. |
| 6,090,932 | A | 7/2000 | McGee et al. |
| 6,107,479 | A | 8/2000 | Natt et al. |
| 6,171,797 | B1 | 1/2001 | Perboast |
| 6,262,251 | B1 * | 7/2001 | Pieken et al. ............... 536/25.3 |

FOREIGN PATENT DOCUMENTS

| | | |
|---|---|---|
| DE | 2931233 | 2/1981 |
| DE | 19935204 | 2/2001 |
| EP | 0 453 247 A2 | 10/1991 |
| EP | 0 294 196 B1 | 3/1996 |
| EP | 0 982 311 A2 | 3/2000 |
| WO | WO 91/06556 | 5/1991 |
| WO | WO 91/10671 | 7/1991 |
| WO | WO 91/13900 | 9/1991 |
| WO | WO 92/06103 | 4/1992 |
| WO | WO 94/13789 | 6/1994 |
| WO | WO 95/24185 | 9/1995 |
| WO | WO 96/34984 | 11/1996 |
| WO | WO97/14706 * | 4/1997 |
| WO | WO 98/30575 | 7/1998 |
| WO | WO 98 30578 A | 7/1998 |
| WO | WO 98 47910 A | 10/1998 |
| WO | WO 01/84234 | 11/2001 |
| WO | WO 01/96357 A2 | 12/2001 |
| WO | WO 02/20541 A2 | 3/2002 |

OTHER PUBLICATIONS

Agrawal and Khorana, (May 1972) J. of the American Chem. Society 94(10): 3579-3585.
Andrus et al. (1988) Tetrahedron Letters 29:861-864.
Bannwarth and Wippler (1990) Helv. Chim. Acta 73:1139-1147.
Bayer and Mutter (1972) Nature 237:512-513.
Beaucage et al. (1992) Tetrahedron 48(12):2223-2311.
Beaucage et al. (1993) Tetrahedron 49(10):1925-19693.
Blackburn et al. (1992) Tetrahedron Letters 34(1): 149-152.
Duggan and Imagire (Feb. 1989) Synthesis 131-132.
Eadie and Davidson (1987) Necleic Acid Reasearch 15(20):8333-8349.
Fischer and Kopczynski (1990) BioTechniques 9:300-301.
Hill et al. (2001) J. Org. Chem. 66:5352-5358.
Johnson et al. (1990) BioTechniques 8:424-428.
March, J., ed. (1992) in *Advanced Organic Chemistry* 839-852.
McBride and Caruthers (1983) Tetrahedron Letters 24(3):245-248.
McBride et al. (1988) BioTechniques 6:362-367.
Micklefield (2001) Current Medicinal Chemistry 8:1157-1179.
Natt and Häner (1997) Tetrahedron 53(28):9629-9636.
Rideout and Breslow (1980) J. Am. Chem. Soc. 102:7816-7817.
Sinha et al. (1983) Tetrahedron Letters 24(52):5843-5846.
Yu et al. (1994) Tetrahedron Letters 35:8565-8568.
Aurup et al. (1992) Biochemistry 31:9636-9641.
Bruick et al. (1996) Chemistry & Biology 3:49-56.
Bruick et al. (1997) Nucleic Acid Res. 25:1309-1310.
Englisch and Gauss(1991) Angew. Chem. Int. Ed. Engle. 30:613-627.
Eritja et al. (1991) Tetrahedron 47: 4113-4120.
Goodchild (1990) Bioconjugate Chemistry 1:166-187.
Giuliano et al. (1993) *J. Org. Chem.* 58:4979-4988.
Giuliano et al. (1990) *J. Org. Chem.* 55:3555-3562.
Gryaznov et al. (1995) Proc. Nat. Acad. Sci. 92:5798-5802.
Haealambidis et al. (1990) Nucleic Acids Res. 18:493-499.
Haralambidis et al. (1987) Tetrahedron Lett. 28:5199-5202.
Hardy et al. (1994) Nucleic Acids Res. 22:2998-3004.
Huryn and Okabe (1992) Chemical Reviews 92:1745-1768.
Jager et al. (1995) *Tetrahedron Letters* 36:861-864.
Jones et al. (1995) J. Med. Chem. 38:2138.
Juby et al. (1991) Tetrahedron Lett. 32:879-822.
Koch et al. (2000) Bioconjugate Cem. 11; 474-483.
Koch et al. (1999) Exiqon.
Krieg et al. (1991) Antisense Res. and Dev. 1:161.
Kumar and Poonian (1984) J. Org. Chem. 49:4905-12.
Leonetti et al. (1990) Bioconjugate Chem. 1:149-153.
Lubineau et al. (1995) *Carbohydrate Research* 270: 163-179.
Ludwig and Eckstein (1989) J. Org. Chem. 54:631-635.
Mikhailopulo et al. (1993) Liebigs Ann. Chem. pp. 513-519.
Mori et al. (1989) Nucleosides & Nucleotides 8:649.
Nishikubo et al. (1981) Tetrahedron Letters 22:3873-3874.
Ono et al. (1995) Nucleic Acids Res. 23:4677-82.
Reddy et al. (1987) Tetrahedron Letters 28:23-26.
Robles et al. (1995) Nucleic Acids Res. 23:4151-61.
Roush et al. (1983) Tetrahedron Letters 24:1377-1380.
Schmidt (1994) Synlett 4:241-242.
Shibuya and Ueda (1980) Chem. Pharm. Bull. 28:939-946.
Sinha and Cook (1988) Nucleic Acids Res. 16:2659.
Smith et al. (1987) Methods in Enzymology, 155:260-301.
Sproat et al. (1987) Nuclic Acids Research 15:6181-6188.
Theisen et al. (1992) Tetrahedron Lett. 33:5033-5036.
Tronchet et al. (1990) Tetrahedron Letters 31:531-534.
Tronchet et al. (1988) Nucleosides & Nucleotides 7:249-269.
Tung (1991) Bioconjugate Chem. 2:464-465.
Verheyden et al. (1971) J. Org. Chem. 36:250-254.
Wagner et al. (1991) Nucleic Acids Res. 19:5965-5971.
Warshaw et al. (1990) J. Med. Chem. 33:1663-1666.
Zalipsky (1995) Bioconjugate Chem. 6:150-165.

* cited by examiner

SEQUENCE LISTING

<160> NUMBER OF SEQ ID NOS: 7

<210> SEQ ID NO 1
<211> LENGTH: 10
<212> TYPE: DNA
<213> ORGANISM: Artificial Sequence
<220> FEATURE:
<223> OTHER INFORMATION: Synthesized

<400> SEQUENCE: 1
tttttttttt                                                          10

<210> SEQ ID NO 2
<211> LENGTH: 4
<212> TYPE: DNA
<213> ORGANISM: Artificial Sequence
<220> FEATURE:
<223> OTHER INFORMATION: Synthesized

<400> SEQUENCE: 2 tttt                                                                 4

<210> SEQ ID NO 3
<211> LENGTH: 9
<212> TYPE: DNA
<213> ORGANISM: Artificial Sequence
<220> FEATURE:
<223> OTHER INFORMATION: Synthesized

<400> SEQUENCE: 3 ttttttttt                                                            9

<210> SEQ ID NO 4
<211> LENGTH: 5
<212> TYPE: DNA
<213> ORGANISM: Artificial Sequence
<220> FEATURE:
<223> OTHER INFORMATION: Synthesized

<400> SEQUENCE: 4 ttttt                                                                5

<210> SEQ ID NO 5
<211> LENGTH: 8
<212> TYPE: DNA
<213> ORGANISM: Artificial Sequence

```
<220> FEATURE:
<223> OTHER INFORMATION: Synthesized

<400> SEQUENCE: 5 tttttttt                                                                8

<210> SEQ ID NO 6
<211> LENGTH: 7
<212> TYPE: DNA
<213> ORGANISM: Artificial Sequence
<220> FEATURE:
<223> OTHER INFORMATION: Synthesized

<400> SEQUENCE: 6 ttttttt                                                                 7

<210> SEQ ID NO 7
<211> LENGTH: 6
<212> TYPE: DNA
<213> ORGANISM: Artificial Sequence
<220> FEATURE:
<223> OTHER INFORMATION: Synthesized

<400> SEQUENCE: 7 tttttt                                                                  6
```

METHODS FOR THE INTEGRATED SYNTHESIS AND PURIFICATION OF OLIGONUCLEOTIDES

This application is a non-provisional of provisional application Ser. No. 60/351,991 filed Jan. 23, 2002.

FIELD OF INVENTION

The present invention relates to the field of nucleotide chemistry. More specifically, the invention relates to the field of oligonucleotide synthesis including purification employing scavenger solid phases.

BACKGROUND OF THE INVENTION

The enormous increase in the demand for synthetic oligonucleotides fueled by the advances in DNA technology over the past few decades has been accelerated by recent progress in sequencing and decoding whole genomes, particularly the human genome. A number of methods in molecular biology and DNA-based diagnostics to amplify, detect, analyze and quantify nucleic acids are dependent on chemically synthesized oligonucleotides. They are employed, for instance, in recombinant host-vector systems used for techniques such as site-directed mutagenesis. They are also employed in PCR methods, which use oligonucleotides as primers in temperature-cycled enzymatic amplifications of nucleic acids. Primers are also needed for state of the art sequencing techniques featuring enzymatic elongation and random termination. A rapidly growing field is the application of oligonucleotides in hybridization assays, which are based on the specific annealing of oligonucleotide probes to the region of a nucleic acid analyte having a complementary sequence. Probes with covalently conjugated dyes generating a fluorescent signal on perfect match hybridization are among the latest developments in this field. Corresponding methods to test for specific genomic epitopes, such as allelic discrimination or SNP detection, employ hybridization probes and are readily multiplexable. Thus, automated high-throughput systems capable of simultaneously screening a vast number of analytes using miniaturized arrays of hybridization probes, such as DNA chips, are used for applications such as genotyping and expression profiling. These and related methods may have an enormous impact in the areas of drug development and health management, as well as other fields.

Antisense technology is another field requiring a rapidly increasing supply of oligonucleotides. Synthetic antisense oligonucleotides are complementary to an RNA or DNA target sequence and are designed to halt a biological event, such as transcription, translation or splicing. They represent a whole new class of therapeutic agents, which have been shown to exhibit antiviral activity by inhibiting viral DNA or protein synthesis and moreover, may be able to cure certain diseases by inhibiting gene expression via specifically recognizing and binding mRNA. The most recent generation of antisense oligonucleotides comprise backbone-modified DNA or RNA derivatives such as 2'-OMe-RNA, phoshorothioate, morpholino nucleic acid, LNA, or combinations thereof. With these derivatives, the properties of antisense compounds, such as nuclease resistance, RNase H susceptibility and binding affinity, which are crucial for either blocking or promoting the degradation of the complementary mRNA, can be modulated and optimized.

Oligonucleotide primers with purities as low as 50% are usually sufficient for standard PCR applications and primers with purities of 70% can be effectively employed in sequencing methods. Other applications, however, generally require purities of greater than 90%. For example, contaminants in an oligonucleotide used as an insert in cloning experiments, after amplification in a host, may dominate the desired product nucleic acid due to their potentially better insertion properties. Antisense oligonucleotides intended for therapeutic purposes have to meet the high standards required by the FDA for drugs applied to humans. To reach purities greater that 90%, the crude product obtained after the cleavage/deprotection step at the end of the synthesis usually has to be subjected to subsequent purification steps, such as HPLC and/or PAGE, depending on the size and the sequence of a desired oligonucleotide.

The current state of the art in oligonucleotide synthesis is automated solid phase synthesis using phosphoramidite chemistry, which in particular is based on the developments of McBride et al. (1983) Tetrahedron Letters 24:245–248 and Sinha et al. (1983) Tetrahedron Letters 24:5843–5846, and which has been, together with related methods such as the hydrogen-phosphonate chemistry, extensively reviewed by Beaucage et al. (1992) Tetrahedron 48:2223–2311, each of which is specifically incorporated herein by reference in its entirety. During solid phase oligonucleotide synthesis, a series of nucleotide monomers are sequentially attached in a predetermined order to either, depending on the direction of chain extension, the 5'-functional group or the 3'-functional group of the growing oligonucleotide strand, which is linked to a solid phase such as CPG or a polystyrene resin. The method for attachment of each monomer is generally comprised of the following steps: 1) deprotection of the reactive functionality, usually the 5'-hydroxyl group, of the growing strand; 2) coupling by addition of a nucleoside monomer and an activator; 3) capping of unreacted terminal functional groups through introduction of an inert protective group, to prevent further coupling to failure sequences; and 4) oxidation of the newly formed internucleosidic phosphorous linkage to the naturally occurring pentavalent state.

This synthetic method has reached a high level of optimization featuring coupling efficiencies of up to 99% on average per cycle. Nevertheless, the small amount of non-extended oligonucleotide strands or failure sequences per cycle results in typical crude yields of about 50–80% for a 20-mer, with further reduced purities for longer oligonucleotides. Even with a highly optimized coupling efficiency of 99%, a 100-mer cannot be obtained in purities exceeding 35%. In the case in which failure sequences subsequently also fail to be capped during the capping step, they continue to participate in the following synthetic cycles. The resulting deletion sequences, ranging from (n–1)-mers and (n–2)-mers to shorter lengths, are present as impurities in the crude full-length oligonucleotide (n-mer). Among these, (n–2)-mers and shorter contaminants are readily removable by chromatographic purification steps, such as HPLC using reverse or anion-exchange phases. However, these methods are unsuitable for separating the (n–1)-mer impurities from the desired (n)-mer. Purification can be achieved by applying PAGE electrophoresis, if the respective low recovery rates are acceptable.

Thus, an effective capping process during the course of every synthetic cycle of an oligonucleotide synthesis is essential for inhibiting failure sequences from undergoing further elongation. In other words, capping allows for the truncation of failure sequences thereby largely reducing the formation of deletion sequences. Since the presence of deletion sequences, having almost identical size and composition as the product, makes purification very difficult, the main utility of capping is to minimize the length and presence of failure sequences.

In current state of the art methods, capping during the course of solid phase phosphoramidite oligonucleotide synthesis is accomplished by acetylation of the 5'-ends of failure sequences employing acetic anhydride in the presence of N-methylimidazole, as described by Eadie et al. (1987) Nucleic Acids Res. 15:8333–8249, which is specifically incorporated herein by reference in its entirety. For oligonucleotide synthesis using the hydrogen-phosphonate approach, Andrus et al. (1988) Tetrahedron Letters 29:861–864, have introduced phosphite monoesters as capping reagents, thus exploiting the coupling chemistry also for the capping reaction. Accordingly, Yu et al. (1994) Tetrahedron Letters 35:8565–8568 (incorporated herein by reference in its entirety), have described the use of diethoxy N,N-diisopropyl phosphoramidite as a capping reagent for a phosphoramidite-based oligonucleotide synthesis. Both of the latter capping methods provide for caps that survive the final cleavage and deprotection of the synthesized oligonucleotide, which is advantageous for applications involving enzymatic reactions capable of excluding the undesired 5'-capped failure sequences e.g. from getting inserted into a vector.

Various strategies comprising capping reagents providing for post-synthetic removal of truncated sequences have been described. For example, the use of lipophilic capping reagents, enabling the separation of capped sequences from the full-length sequences on a hydrophobic stationary phase has been described by Natt et al. (U.S. Pat. No. 6,107,479 and Tetrahedron 53:9629–9636 (1997)). Since this purification step is based on unspecific, non-covalent interactions it relies on time-consuming chromatographic techniques, which are hardly suited for automation. Thus, it is not a substantial improvement over standard procedures, for instance RP-HPLC purification subsequent to processing the oligonucleotide synthesis without removal of the DMT-group in the final synthetic cycle ('trityl-on'). Coolidge et al., U.S. Pat. No. 5,464,759, have described the use of capping reagents bearing an antigenic site. Following oligonucleotide synthesis and cleavage from the solid support, the crude product is eluted through a resin that is derivatized with the corresponding antibodies. Due to the specific immunological interaction, the truncated contaminants are removed and a purified product is obtained. Coolidge et al. do not convincingly teach, however, how to bind the cap including the antigenic site to the failure sequences in such a manner that it can survive the final cleavage/deprotection step. Both deprotection and intact caps are crucial for the post-synthetic purification step intended by the authors. Furthermore, the application of antibodies requires highly skilled personnel and lacks cost efficiency.

Coolidge et al., have also suggested the post-synthetic immobilization of contaminants using capping reagents comprising a functionality that is able to covalently bind to a correspondingly derivatized matrix. Coolidge et al., however, do not teach how to accomplish this method of purification.

SUMMARY OF THE INVENTION

The present invention includes novel methods for the integrated synthesis and purification of oligonucleotides. Included in the present invention are novel capping reagents, which enable a simple and rapid post-synthetic purification step. The methods employ chemical purification handles based on cycloaddition chemistry, particularly Diels-Alder chemistry in aqueous solutions that reduce or even eliminate the need for cumbersome purification steps such as preparative RP-HPLC, PAGE electrophoresis and/or AX-chromatography, all of which are time-consuming and laborious procedures requiring highly skilled personnel and are difficult to automate for high-throughput formats.

The method of the present invention for the integrated synthesis and purification of oligonucleotides comprises the steps of:

1. Synthesizing an oligonucleotide pursuant to standard techniques for solid phase oligonucleotide synthesis (SPOS) known in the art, wherein during the capping step of each synthetic cycle a cap derivatized with a moiety capable of undergoing a cycloaddition reaction is introduced to unreacted terminal functional groups of the growing oligonucleotide chain which failed to be elongated in the preceding coupling step, wherein the corresponding capping agent comprises functional groups A and B, functional group A being reactive to terminal functional groups of the oligonucleotide and functional group B being able to participate in a cycloaddition reaction. Said caps are characterized in that they are stable during the synthesis and the work-up of the oligonucleotide. In a preferred embodiment the cap is derivatized with a moiety capable of undergoing a Diels-Alder reaction.

2. Cleaving the oligonucleotide from the solid support and deprotecting according to standard techniques for SPOS known in the art, to provide a mixture of the full-length oligonucleotide product and contaminant truncated sequences.

3. Adding a trapping agent to the mixture obtained following step 2, to provide a mixture of the trapping agent/contaminant truncated sequences and an aqueous solution of the full length oligonucleotide product. This mixture will also contain a lower concentration of the truncated contaminant sequences as in step 2.

4. Separating the trapping agent/contaminant truncated sequences, preferably by filtration from the remainder of the reaction mixture, yielding a filtrate which contains the full length oligonucleotide product with a much lower concentration of truncated contaminant sequences as in step 2, thus a purified oligonucleotide.

The methods of this invention can be applied to any solid phase oligonucleotide synthetic schemes including, but not limited to phosphoramidite chemistry, H-phosphonate chemistry, or any other synthetic methods used to prepare oligonucleotides on solid supports.

The present invention includes methods for the preparation of oligonucleotides, as well as, methods for the purification of oligonucleotides. The methods are based on the trapping and therefore the removal of truncated sequences during the course of the oligonucleotide preparation, as outlined in FIGS. 1 and 2. Additionally, the invention includes methods for the synthesis and application of novel capping reagents. According to the invention, these capping reagents provide for the attachment of functional groups that are capable of undergoing cycloaddition reactions, particularly Diels-Alder reactions to the terminus of failure sequences in the capping steps during the synthesis of oligonucleotides. Upon completion of the oligonucleotide synthesis a crude oligonucleotide product is obtained, which contains the desired full-length oligonucleotide together with the capped truncated sequences. The truncated sequences are then removed by reaction with a trapping agent in aqueous solution. The trapping agent is characterized in that it is derivatized with functional groups, such as dienophiles, that are able to react with the functional groups introduced on the truncated sequences, such as dienes, in a Diels-Alder reaction. Thus, by facile removal of the trapping agent loaded with the truncated contaminant oligonucleotides employing suitable methods known by those skilled in the art, such as filtration, a purified solution of the product oligonucleotide is obtained. FIG. 1 illustrates the principle of the trapping process as described above exemplified by one possible embodiment in which hexadienyl phosphodiester groups are introduced as caps to failure sequences and a maleimide-derivatized solid phase is used as the trapping agent.

In one embodiment of the invention, the functional groups introduced to the failure sequences are dienes and the corresponding chemical moieties attached to the trapping agent are dienophiles. In another embodiment of the invention, the functional groups introduced to the failure sequences are dienophiles and the corresponding chemical moieties attached to the trapping agent are dienes. The method of this invention is not limited to the Diels-Alder reaction, however, but rather can be extended to any cycloaddition reaction by choosing the appropriate capping/trapping agents.

The methods disclosed in this invention are applicable to solid phase oligonucleotide synthetic schemes in which the growing oligonucleotide chain is built in 3'-5' direction, as well as, in solid phase oligonucleotide synthetic schemes in which the growing oligonucleotide chain is built in 5'-3' direction. The methods are applicable with or without removing the final terminal protective group during the synthesis of the oligonucleotide thus, in the latter case, enabling the use of the terminal protective group as a handle in additional purifications, as exemplified by employing the commonly used terminal dimethoxytrityl group as a handle in a reversed-phase cartridge based second purification.

The novel methods and capping reagents of this invention have significant advantages and do not suffer from the limitations inherent to the prior art methods and capping reagents. The capping reagents described herein provide for a smooth and efficient capping process, stable capping as well as simple, rapid and specific trapping of contaminant sequences. They can easily be adopted in syntheses of modified oligonucleotides, such as phosphorothioates, RNA derivatives and locked nucleic acids (LNA), and oligonucleotides conjugated to one or several dyes via a linker unit. The methods and capping reagents, due to the simple and generally applicable trapping process described in the invention, are highly suitable for an automated setup.

BRIEF DESCRIPTIONS OF THE DRAWINGS

Figure 4:
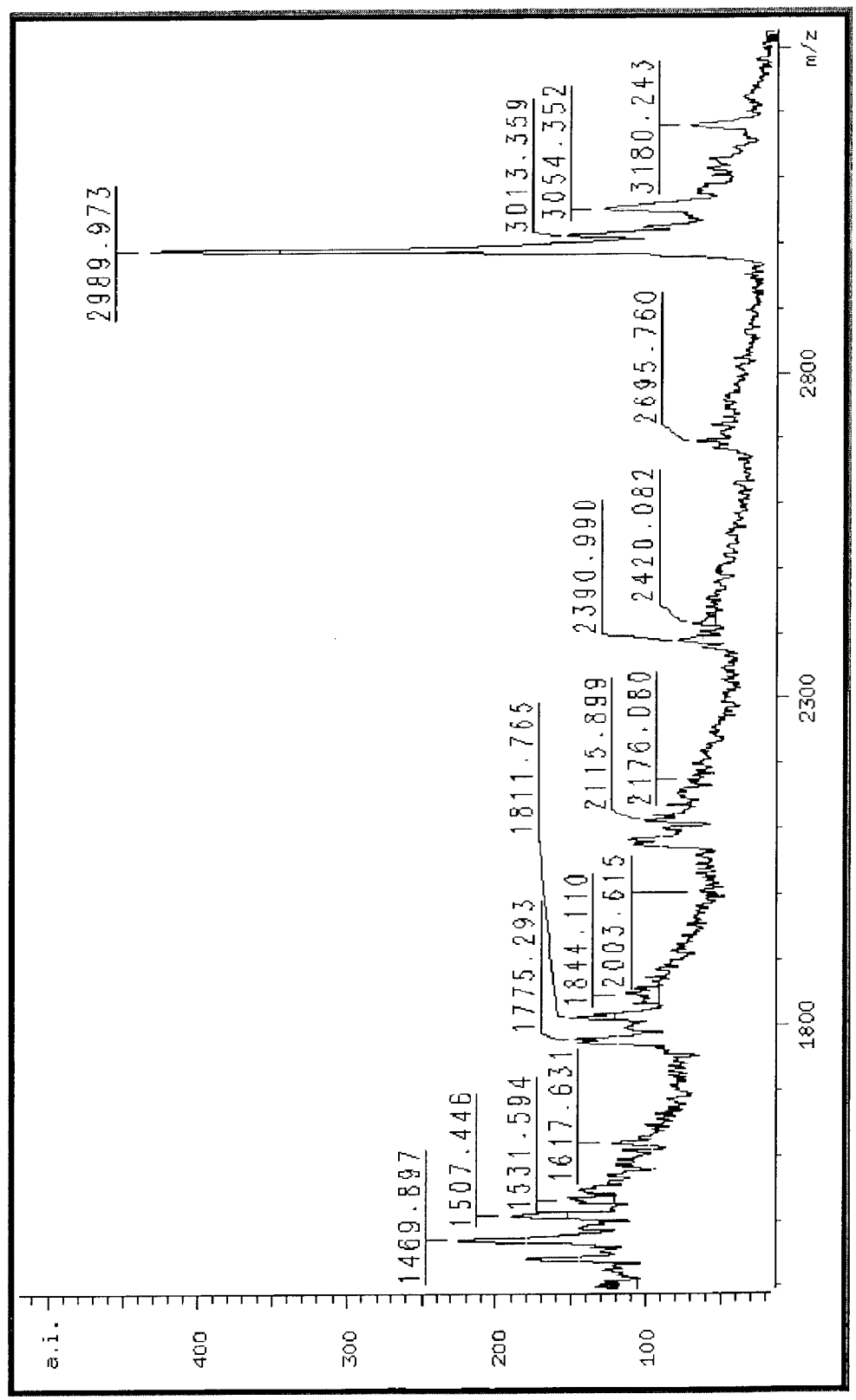

FIG. 4 displays the MALDI-MS spectrum of crude oligonucleotide (32) prepared as described in Example 5.

Figure 5:
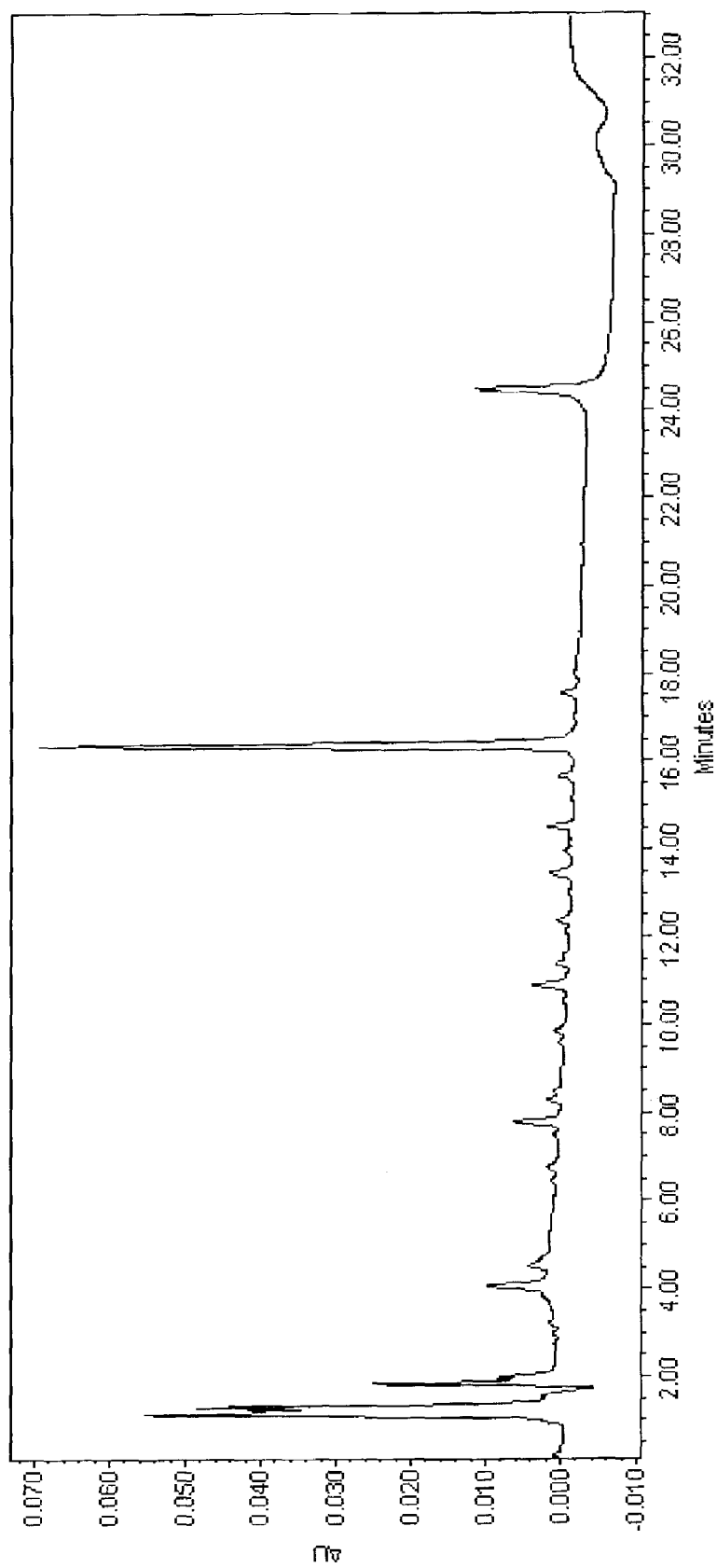

FIG. 5 shows the anion-exchange HPLC chromatogram of the purified oligonucleotide (32) resulting from the trapping experiment employing maleimide CPG (40) as described in Example 6.

Figure 6:
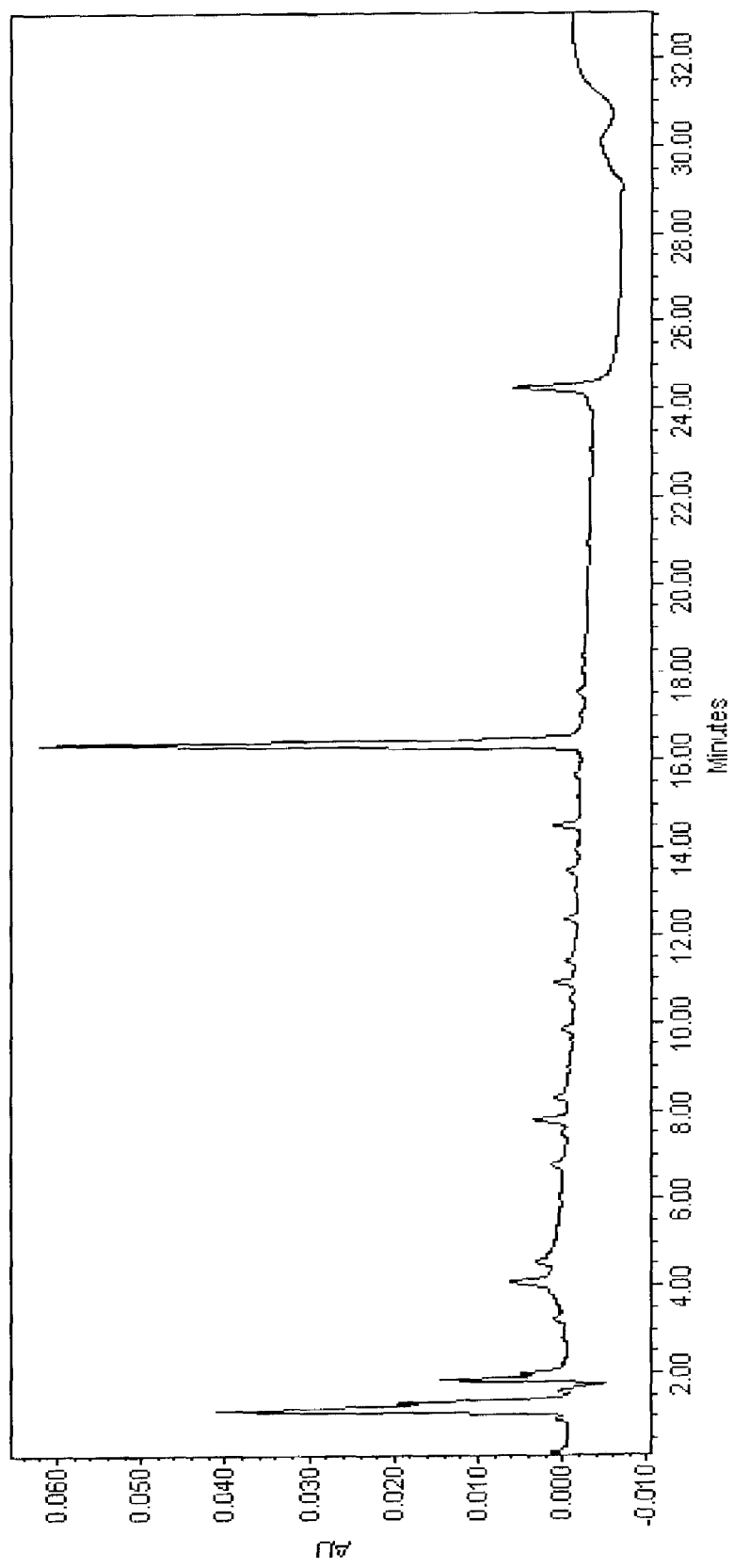

FIG. 6 shows the anion-exchange HPLC chromatogram of the purified oligonucleotide (32) resulting from the trapping experiment employing maleimide silica gel (41) as described in Example 6.

DETAILED DESCRIPTION OF THE INVENTION

Various terms are used herein to refer to aspects of the present invention. To aid in the clarification of the description of the components of the invention, the following descriptions are provided.

It is to be noted that the term "a" or "an" entity refers to one or more of that entity; for example, an oligonucleotide refers to one or more oligonucleotides. As such, the terms "a" or "an," "one or more" and "at least one" are used interchangeably herein.

"Oligonucleotide synthesis" as used herein refers to any method of solid phase oligonucleotide synthesis (SPOS) known to those skilled in the art. In a preferred embodiment "oligonucleotide synthesis" includes, but is not limited to either phosphoramidite, phosphotriester and/or nucleoside hydrogen phosphonate chemistries known to those skilled in the art as described e.g. by Gait, ed., "Oligonucleotide synthesis: A practical approach" (1984) IRL Press, Oxford, UK; Eckstein, ed., "Oligonucleotides and analogs: A practical approach" (1991) IRL Press, Oxford, UK; Beaucage et al. (1992) Tetrahedron 48:2223–2311; McBride and Caruthers (1983) Tetrahedron Letters 24:245–248 and Sinha et al. (1983) Tetrahedron Letters 24:5843–5846, each of which is specifically incorporated herein by reference in its entirety, or any other chemistry used in solid phase oligonucleotide synthesis. Typically, oligonucleotide synthesis involves a number of chemical steps that are performed in a cyclical repetitive manner throughout the synthesis, each cycle adding one nucleotide to the growing oligonucleotide chain. The chemical steps involved in a cycle include a deprotection step that liberates a functional group on the oligonucleotide for further chain elongation, a coupling step that incorporates a nucleotide into the growing oligonucleotide chain, a capping step as defined below, and other steps as required by the particular chemistry used in the oligonucleotide synthesis, e.g. an oxidation step as required with phosphoramidite chemistry. The extension of the oligonucleotide chain in the course of oligonucleotide synthesis is usually pursued in the 3' to 5' direction by adding nucleoside monomers carrying a suitable protective group at the 5'-position, usually a DMT-group, and a suitable activating group, e.g. a phosphoramidite group, at the 3'-position intended to form the linkage to the 5'-position of the growing chain. In some instances, such as the synthesis of oligonucleotides with a N3'-P5' phosphoramidite internucleosidic linkage, the chain assembly is preferably performed in 5' to 3' direction. The respective mononucleosidic building blocks carry a suitable protecting group at the 3'-position and the activating group at the 5'-position.

As used herein the term "oligonucleotide" refers to a single stranded chain of either deoxyribonucleotides or ribonucleotides or chemical modifications thereof, such as e.g. nucleotides with a 2'O-4'C-methylene bridge in their sugar portion, which are the nucleotides that make up locked nucleic acids (LNA). Modifications include, but are not limited to, those that provide other chemical groups that incorporate additional charge, polarizability, hydrogen bonding, electrostatic interaction, and functionality to the individual nucleotides or their corresponding bases or to the oligonucleotides as a whole. Such modifications include, but are not limited to, modified bases such as 2'-position sugar modifications, 5-position pyrimidine modifications, 8-position purine modifications, modifications at cytosine exocyclic amines, substitution of 5-bromo-uracil; backbone modifications, methylations, bases that can be part of unusual base-pairing combinations such as the isobases isocytidine and isoguanidine and the like. Modifications further include attached labels and reporter molecules, such as fluorescent dyes, biotin, minor groove binders and the like that are known to those skilled in the art. In addition modifications include modified backbones of the oligonucleotides, examples being peptide nucleic acids (PNA), phosphorothioate DNA, methylphosphonate DNA and other modifications known to those skilled in the art as reviewed by Micklefield (2001) Current Medicinal Chemistry 8:1157–1179, which is specifically incorporated herein by reference in its entirety. Oligonucleotides, as referred to in this invention can consist of any combinations of the nucleotides and their modifications described above and can have either a few, e.g. up to 20, or many, e.g. 20 to several hundred or more, nucleotides incorporated in their chain, the total number of nucleotides being denoted n in the context of this invention.

A "failure sequence" refers to an oligonucleotide chain, which failed to be elongated in a coupling step. Failure sequences are typically capped in solid phase oligonucleotide synthesis and thereby converted to truncated sequences. Truncated sequences account for contaminant derivatives as defined below with chain lengths from 1 to n−1.

"Capping" and "capping step" as used herein, refer to reacting the free hydroxyl group, or any other functional group suitable for chain extension, of an oligonucleotide chain with a capping reagent during solid phase oligonucleotide synthesis to render the chain incapable of participating in subsequent coupling steps. Capping can be performed either on the 5'-functional group of a 3' to 5' extended oligonucleotide or on the 3'-functional group of a 5' to 3' extended oligonucleotide. Capping steps are performed in between the coupling step of the solid phase oligonucleotide synthesis and the next deprotection step. The capping reagents of the embodiments of this invention comprise functional groups that allow the post-synthetic removal of contaminant oligonucleotides, as defined below.

As used herein, the term "cap" refers to the chemical group which is introduced on a failure sequence during a capping step in oligonucleotide synthesis.

The terms "contaminant oligonucleotides" and "contaminant derivatives" are used interchangeably to refer to the oligonucleotides formed during the SPOS that are not comprised of the desired number and/or the desired sequence of nucleotide monomers. Contaminant oligonucleotides and contaminant derivatives therefore represent impurities in the synthesized oligonucleotide.

The term "cycloaddition" as used herein refers to a reaction in which unsaturated molecules combine to form rings. The method of this invention can be extended to all 4n and 4n+2 cycloaddition reactions (wherein n=1, 2, 3, 4, etc.). Examples of cycloaddition reactions include, but are not limited to, the Diels-Alder reaction, 1,3-dipolar cycloaddition reactions, the ene reaction and [2+2] cycloadditions (a 4n type reaction), such as ketene additions and photochemical [2+2] additions. In a preferred embodiment the cycloaddition reaction is a Diels-Alder reaction.

The term "Diels-Alder reaction" as used herein refers to a cycloaddition reaction between a conjugated diene and an unsaturated molecule to form a cyclic compound with the $\pi$-electrons being used to form the new $\sigma$-bonds. The Diels-Alder reaction is an example of a [4+2] cycloaddition reaction, as it involves a system of $4\pi$-electrons (the diene) and a system of $2\pi$-electrons (the dienophile). The reaction can be made to occur very rapidly, under mild conditions and for a wide variety of reactants. The Diels-Alder reaction is broad in scope and well known to those knowledgeable in the art. A review of the Diels-Alder reaction is given by March, ed., *Advanced Organic Chemistry* (1992) John Wiley & Sons, NY, pp. 839–852, which is specifically incorporated herein by reference in its entirety.

"Trapping" refers to the attachment of contaminant oligonucleotides to a solid phase, herein denoted "trapping agent," via a covalent bond.

The term "trapping agent" as used herein refers to a solid phase that is derivatized with a moiety capable of undergoing a cycloaddition reaction with the corresponding functional groups introduced to the contaminant oligonucleotides via capping. In the case of a Diels-Alder cycloaddition reaction the solid phase is derivatized either with diene or dienophile moieties depending on the corresponding functional groups introduced to contaminant oligonucleotides via capping. Said derivatizations are accomplished by attaching said moieties to functional groups on the solid phase. These functional groups include, but are not limited to, alcohols, amines, carboxylates, sulfonic acids and halides.

A "solid phase" as used herein refers to a resin, membrane or polymer that is insoluble in the medium employed in a particular reaction or unit operation performed to synthesize or purify oligonucleotides. A solid phase can be of inorganic nature, including, but not limited to inorganic oxides such as silica, alumina, zeolites and controlled pore glass, or of organic nature, including, but not limited to polystyrene, polyacrylamide, polymetbacrylate, polyvinylalcohol, other synthetic polymers, carbohydrates such as cellulose and starch or other polymeric carbohydrates, or other organic polymers and any copolymers, composite materials or combination of the above inorganic or organic materials. Furthermore, a solid phase can be comprised of a soluble polymer that can be forced to undergo a phase transition, e.g. polyethylene glycol and derivatives thereof, as described e.g. by Bayer et al. (1972) Nature 237:512–513, which is incorporated herein by reference in its entirety.

The present invention includes a method for the integrated synthesis and purification of oligonucleotides comprising the steps of:

1. Synthesizing an oligonucleotide pursuant to standard techniques for SPOS known in the art, wherein during the capping step of each synthetic cycle a cap derivatized with a moiety capable of undergoing a cycloaddition reaction is introduced to unreacted terminal functional groups of the growing oligonucleotide chain which failed to be elongated in the preceding coupling step. Said caps are selected such that they are stable during the synthesis and the work-up of the oligonucleotide. The terminal protective group of the oligonucleotide may or may not be removed within this step. In a preferred embodiment the cap is derivatized with a moiety capable of undergoing a Diels-Alder reaction. Thus, in one embodiment of the present invention the cap is derivatized with a diene and in another embodiment, the cap is derivatized with a dienophile.

2. Cleaving the oligonucleotide from the solid support and deprotecting according to standard techniques for SPOS known in the art, e.g. by incubation with ammonia. A mixture of the full-length oligonucleotide product and contaminant truncated sequences is obtained in this step. Following cleavage from the solid support the reaction mixture is concentrated at least partially or completely under reduced pressure to remove solvents and volatile reagents. Either a partially concentrated solution or a solid residue is obtained and a suitable aqueous buffer is then added to the residual solution or the solid residue.

3. Adding a trapping agent to the buffered solution obtained following step 2, to provide after reaction a mixture of the trapping agent/contaminant truncated sequences and an aqueous solution of the full length oligonucleotide product. Upon addition of the trapping agent the mixture is incubated under appropriate conditions for the intended trapping process, i.e. an aqueous Diels-Alder reaction. The reaction mixture obtained will also contain a much lower concentration of truncated contaminant sequences which fail to react with the trapping reagent.

4. Separating the trapping agent, preferably by filtration from the remainder of the reaction mixture, yielding a filtrate which contains the full length oligonucleotide product with a much lower concentration of truncated contaminant sequences as in step 2, thus the purified oligonucleotide.

The methods of this invention can be applied to any solid phase oligonucleotide synthetic schemes including, but not limited to phosphoramidite chemistry, H-phosphonate chemistry, or any other synthetic methods used to prepare oligonucleotides on solid supports.

This invention includes methods for the synthesis and use of novel capping reagents in the solid phase synthesis of oligonucleotides. The capping reagents of this invention are comprised of two functional groups, one of which effects capping and is denoted herein as a type A functional group, and the other of which is capable of undergoing a cycloaddition reaction and is denoted as a type B functional group. In a preferred embodiment of this invention the cycloaddition reaction is a Diels-Alder reaction.

The capping reagents of this invention are generally depicted as follows:

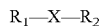

wherein $R_1$ is a functional group of type A;

$R_2$ is a functional group of type B; and

X is an optional spacer unit including, but not limited to, a group selected from alkenyl, diacyl, oligoethylene glycol, or any combinations thereof, or any other chemical moiety known in the art suitable for linking functional groups without interfering with the processes involved in the oligonucleotide synthesis and purification as described herein. In one embodiment of the invention said spacer X, as part of the cap, may have a promoting effect especially on the trapping reaction, due to its properties such as its shape, flexibility, polarity and solubility. Thus, by modulating the design of the spacer unit for specific synthetic applications the trapping process as described herein can be optimized and tailored to any particular chemistry employed in a solid phase oligonucleotide synthesis.

Functional groups of type A are selected based upon their ability to react in a fast and selective manner with the unprotected terminal functional groups of failure sequences. These attributes generally qualify for an automated setup of an oligonucleotide synthesis with typical capping times of 30 seconds to 30 minutes, preferably of 30 seconds to 5 minutes. Furthermore, type A functional groups are selected to provide for capping reactions that do not require additives and do not promote by-products that interfere with either the synthetic processes involved in the oligonucleotide synthesis or with the growing oligonucleotide chain. The linkages generated in the capping steps must remain stable during all steps of the synthetic cycles in solid phase oligonucleotide synthesis and during the cleavage/deprotection procedure performed after chain assembly. When used with phosphoramidite chemistry, type A functional groups are selected to exhibit stability against the typical detritylation agent dichloroacetic acid, as well as against aqueous ammonia under elevated temperature.

Various methods of applying type A functional groups for creating linkages that meet the above mentioned requirements are known to those skilled in the art. In a preferred embodiment, type A functional groups are selected from the group including, but not limited to compounds represented by the following general structures: a carbamate (1), a phosphite diester (2), which is oxidized to a more stable phosphate diester (2') during the course of a solid phase oligonucleotide synthesis, and a phosphite triester (3), which is oxidized to a more stable phosphate triester (3') during the course of a solid phase oligonucleotide synthesis.

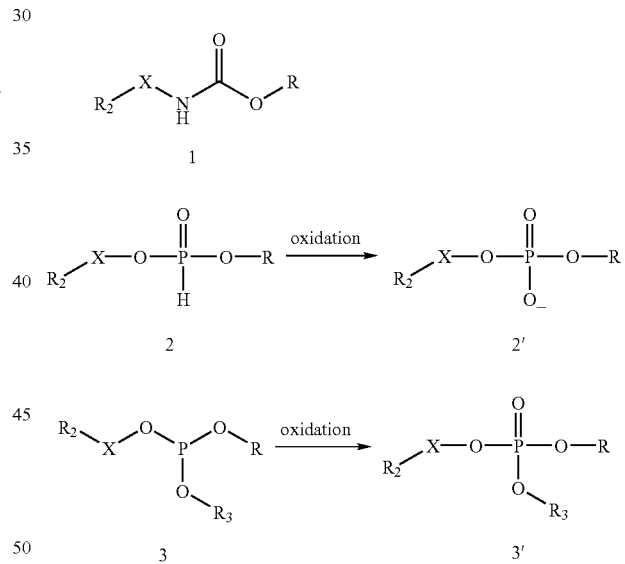

wherein

R is the terminus of a capped oligonucleotide;

$R_2$ is a type B functional group;

$R_3$ is a protecting group selected from the group including, but not limited to 2-cyanoethyl, methyl, allyl, or any other phosphorus protecting group used in oligonucleotide synthesis known to those skilled in the art; and X is an optional spacer unit selected from the group consisting of alkenyl, diacyl, oligoethylene glycol, any combinations thereof, or any other chemical moiety known in the art suitable for linking functional groups without interfering with the processes involved in the oligonucleotide synthesis and purification as described herein.

More specifically, type A functional groups are selected from the group including, but are not limited to compounds represented by the general formulas (4), (5) and (6) below:

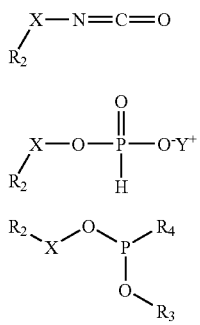

wherein $R_2$ is a type B functional group;

$R_3$ is a protecting group selected from the group including, but not limited to 2-cyanoethyl, methyl, allyl, or any other phosphorus protective group used in oligonucleotide synthesis known to those skilled in the art;

$R_4$ is a dialkylamino, wherein said alkyl group has from one to about six carbons, e.g. diisopropylamino, diethylamino, dimethylamino or $R_4$ is a cyclic substituent attached via a nitrogen atom that is part of the ring system, the ring system containing from 4 to 7 carbons and up to 3 heteroatoms, e.g. pyrrolidino, piperidino, morpholino or alkyl substituted derivatives thereof;

X is an optional spacer unit selected from the group consisting of alkenyl, diacyl, oligoethylene glycol, any combinations thereof, or any other chemical moiety known in the art suitable for linking functional groups without interfering with the processes involved in the oligonucleotide synthesis and purification as described herein; and Y is ammonium, lower alkylammonium, such as triethylammonium, tetrabutylammonium, diisopropylammonium, cyclohexylammonium and diisopropylethylammonium, pyridinium, lutidinium or a metal salt cation.

Capping reagents having the general formula (4), employ isocyanate groups as type A functional groups, which create carbamate linkages upon reaction with hydroxyl groups at the termini of the failure sequences, as illustrated by compounds of the general formula (1) above. Examples of the reaction of isocyanates with hydroxyl groups are provided by Duggan and Imagire (1989) Synthesis pp. 131–132 and Agarwal and Khorana (1972) J. Am. Chem. Soc. 94:3578–3585, each of which is specifically incorporated herein by reference in its entirety.

In another embodiment, the capping reagent contains a phosphite monoester moiety represented by compounds having the general formula (5) (a hydrogen phosphonate), which enables binding to a failure sequence via a phosphite diester linkage as illustrated by compounds of the general formula (2). The underlying capping reaction is especially useful in the context of the "H-phosphonate" approach to oligonucleotide synthesis as described by Andrus et al., EP Patent No. 0,294,196 B1, which is incorporated herein by reference in its entirety. To permit the reliable automation of the procedure, adamantoyl chloride is recommended as an activating reagent by Andrus et al. (1988) Tetrahedron Letters 29:861–864, which is incorporated herein by reference in its entirety. Andrus et al. have demonstrated the usefulness of capping reagents based on H-phosphonate chemistry, but have not described the introduction of a type B functional group with the capping reagents employed in their disclosures.

In the most preferred embodiment of the present invention, phosphoramidite groups as illustrated by compounds of the general formula (6) are employed as the type A functional group of the capping reagent, creating a phosphite triester linkage as represented by compounds of the general formula (3) above. Processes for preparing caps of general formula (3) are well known in the art, as reviewed by Beaucage and Iyer (1992) Tetrahedron 48:2223–2311, which is incorporated herein by reference in its entirety. For example, the capping reagent illustrated by general formula (3) can be obtained by reacting the phosphitylating reagent of formula (6), wherein $R_4$ is e.g. a diisopropylamino group and $R_3$ is e.g. a 2-cyanoethyl group, in the presence of an activator such as 1H-tetrazole or 4,5-dicyanoimidazole in a suitable solvent with the terminal hydroxyl group of a failure sequence.

The approach using phosphoramidite derivatives of formula (6) as capping reagents is highly advantageous when phosphoramidite chemistry is employed to promote the chain elongation in the solid phase oligonucleotide synthesis. In this case, a common activator can be used for both the coupling and the capping steps, thus eliminating the need for washing steps between the coupling reaction and the capping reaction. Furthermore, in this particular case no extra reagent flasks need to be introduced at a given automated oligonucleotide synthesizer and cross-reactivities that are potentially introduced through the use of different chemistries in one synthesis are excluded.

Both, the phosphite triester and the phosphite diester derivatives, as generated by the two latter variants of the above described type A functional groups are transformed into stable P(V)-derivatives, i.e. the phosphate triester (3') and the phosphate diester (2'), respectively, in the oxidation step that is employed after the capping step in conventional protocols for oligonucleotide synthesis.

The present invention also includes methods for the synthesis of the capping reagents described herein. In particular, the preparation of capping reagents having a phosphoramidite derived type A functional group according to formula (6) is described. Processes for synthesizing such compounds are known in the art as reviewed by Beaucage and Iyer (1993) Tetrahedron 49:1925–1963, which is incorporated herein by reference in its entirety. In a preferred embodiment, a compound of formula (6) is obtained by reacting an alcohol of formula (7), comprising a type B functional group ($R_2$) and an optional spacer unit (X), with the phosphitylating reagent of formula (8):

$$R_2-X-OH \qquad 7$$

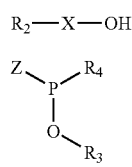

wherein $R_2$ is a type B functional group;

$R_3$ is a protecting group selected from the group including, but not limited to 2-cyanoethyl, methyl, allyl, or any other phosphorus protective group used in oligonucleotide synthesis known to those skilled in the art;

$R_4$ is dialkylamino group, wherein said alkyl groups have from one to about six carbons, e.g. diisopropylamino, diethylamino, dimethylamino, or $R_4$ is a cyclic substituent attached via a nitrogen atom that is part of the ring system, the ring system containing from 4 to 7 carbons and up to 3 heteroatoms, e.g. pyrrolidino, piperidino, morpholino, or alkyl substituted derivatives thereof;

X is an optional spacer unit selected from the group including, but not limited to alkenyl, diacyl, oligoethylene glycol, any combinations thereof, or any other chemical moiety known in the art suitable for linking functional groups without interfering with the processes involved in the oligonucleotide synthesis and purification as described herein; and Z is a halide, such as chloride or $R_4$.

In one embodiment, a compound of formula (6) is obtained by reacting the phosphitylating reagent of formula (8), with a chloride as substituent Z, with an alcohol of formula (7) in the presence of a tertiary amine, such as diisoproylethylamine, in a suitable solvent and by applying proper reaction conditions known to those skilled in the art.

In another embodiment, a compound of formula (6) is obtained by reacting the phosphitylating reagent of formula (8), wherein Z is a diisopropylamino substituent, with an alcohol of formula (7) in the presence of an activator, e.g. 1H-tetrazole or 4,5-dicyanoimidazole, or other activators known to those skilled in the art, in a suitable solvent and by applying proper reaction conditions known to those skilled in the art.

The post-synthetic method for trapping and subsequent removal of contaminant oligonucleotides, is based on the incorporation of functional groups into said oligonucleotides, which serve as anchor points for the immobilization to a trapping agent. Such functional groups, referred to herein as type B functional groups, are attached to failure sequences during the course of the capping step of the oligonucleotide synthesis via the novel capping reagents as described herein. Type B functional groups are functional groups that can participate in a cycloaddition reaction, preferably a Diels-Alder reaction. Said trapping agent on the other hand is derivatized with a chemical moiety that, subsequent to the removal of the oligonucleotides from the solid phase, can be reacted with the type B functional group of the contaminant oligonucleotides in a cycloaddition reaction, preferably a Diels-Alder reaction to promote the formation of a covalent bond between the contaminant oligonucleotides and the trapping agent. The chemical moiety of the trapping agent is denoted herein as a type C functional group. The type B functional group can be any group that is capable of reacting selectively with the type C functional group in a cycloaddition reaction, preferably a Diels-Alder reaction. Type B functional groups must be inert and remain unaffected during the chemical processes involved in the solid phase oligonucleotide synthesis, including the basic cleavage of the synthesized oligonucleotide from the solid phase. In one embodiment, Type C functional groups are selected from the group including, but not limited to conjugated dienes, such as alkyldienes, cyclohexadienes, furans, beta-Ionol, and derivatives thereof.

Cycloaddition reactions, particularly the Diels-Alder reaction, are uniquely suited for establishing the linkage between contaminant oligonucleotides and a trapping agent. The Diels-Alder cycloaddition is highly chemoselective and only suitably electronically configured diene and dienophile pairs will react. The reaction proceeds under mild conditions in a reasonable time frame. Furthermore Diels-Alder reactions are accelerated by aqueous solvents and can be performed in such media at relatively low temperatures giving high conversion rates without significant formation of side-products, as exemplified by Rideout and Breslow (1980) J. Am. Chem. Soc. 102:7816–7817, which is incorporated herein by reference in its entirety. Aqueous Diels-Alder reactions were favorably applied to oligonucleotides by Hill et al. (2001) J. Org. Chem. 66:5352–5358, which is incorporated herein by reference in its entirety.

The trapping agents of this invention are comprised of a solid phase, as defined above, which is derivatized with a moiety that can undergo a cycloaddition reaction. In a preferred embodiment, the cycloaddition reaction is a Diels-Alder reaction and the solid phase is therefore derivatized either with diene or dienophile moieties as illustrated by formula (9):

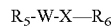

wherein $R_5$ represents the solid phase;

$R_6$ is a type C functional group, as applied to a Diels-Alder reaction $R_6$ is selected from the group consisting of a diene or dienophile. In one embodiment $R_6$ is selected from the group including, but not limited to conjugated dienes, such as alkyldienes, cyclohexadienes, furans, beta-Ionol, and derivatives thereof.

X is an optional spacer unit selected from the group consisting of alkenyl, diacyl, oligoethylene glycol, any combinations thereof, or any other chemical moiety known in the art suitable for linking the moiety $R_6$ to a solid phase that is compatible with the trapping process as described herein; and W is the chemical moiety generated by the derivatization of the functional group on the solid phase and is selected from the group including, but not limited to O, NH, NH(CO)O, NH(CS)O, NH(CO)NH, NH(CO), (CO)NH and a moiety derived from introducing silyl groups on the solid phase, including, but not limited to $O_3Si$ (three linkages to the solid phase), $O_2(R_7)Si$ (two linkages to the solid phase), $O(R_7)_2Si$ (one linkage to the solid phase);

wherein $R_7$ is selected from the group consisting of a C1–C20 alkyl group.

The attachment sites of the W substituents on the solid phase are positioned on the surface of the solid phase, in case of a silica support or a CPG support, or in the interior of the solid phase, in case of a polystyrene resin. The scope of the chemical moiety W is limited only by the fact that it must be inert during the trapping process and its formation must be compatible with the type C functional group, the spacer X and the solid phase used.

Methods to derivatize CPG and organic polymeric solid phases with moieties capable of undergoing Diels-Alder reactions have been described by Pieken et al., U.S. patent application Ser. No. 09/845,742, filed May 1, 2001, entitled "Method For Immobilizing Oligonucleotides Employing the Cycloaddition Bioconjugation Method," which is incorporated herein by reference in its entirety. Derivatized solid phases obtained accordingly are suitable as trapping agents as defined herein.

Example 1 describes the preparation of a CPG solid phase that is suitable as a trapping agent using the method of the present invention. Specifically, Example 1 describes the derivatization of CPG with maleimide-silane reagent (10), which serves as the dienophile in a Diels-Alder reaction within the trapping process. Scheme 1 outlines the synthesis of the functionalized silane reagent (10) suitable for said derivatization of CPG by reaction of propylaminosilane (11) with the activated compound (12).

Scheme 1

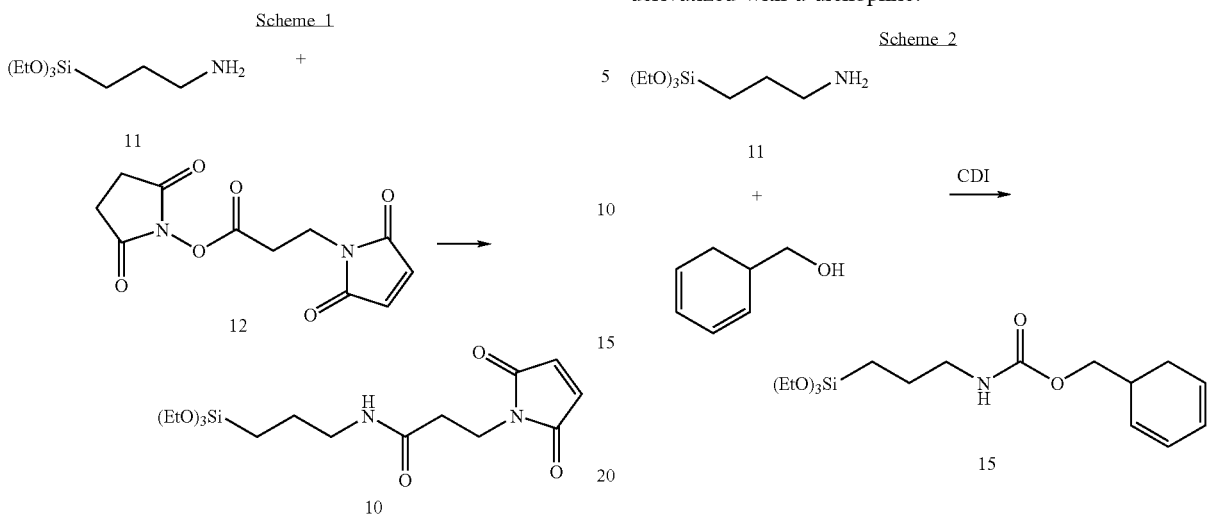

Upon treatment of CPG with reagent (10), the maleimide moieties are readily attached to the glass surface resulting in the said derivatization of the CPG as illustrated by formula (13).

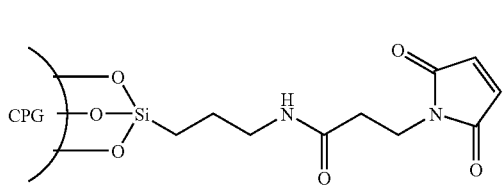

Example 2 describes the preparation of a second type of maleimide derivatized CPG, which is also suitable as a trapping agent using the method of this invention. Specifically, Example 2 describes the derivatization of CPG with maleimide-silane reagent (14), which is prepared by the reaction of compound (11) with maleic anhydride as described by Gunther et al., European Pat. No. 0,982,311 A2, which is incorporated herein by reference in its entirety. The attachment of reagent (14) to the surface of the CPG particles is accomplished using the method described in Example 1, yielding structures analogous to formula (13).

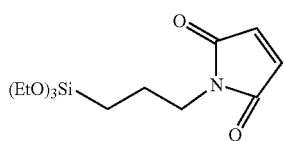

The derivatization of CPG with a diene moiety has been described by Pieken et al., U.S. patent application Ser. No. 09/845,742, filed May 1, 2001, entitled "Method For Immobilizing Oligonucleotides Employing the Cycloaddition Bioconjugation Method," which is incorporated herein by reference in its entirety. The synthesis of reagent (15), which is derivatized with a cyclohexadiene moiety is illustrated in Scheme 2. The attachment of reagent (15) to the surface of the CPG particles is accomplished using the method described in Example 1 for the attachment of compound (10) to CPG. The resulting diene-modified CPG serves as trapping agent according to the method of this invention, immobilizing truncated oligonucleotides, which carry a cap derivatized with a dienophile.

Scheme 2

Pieken et al., U.S. patent application Ser. No. 09/845,742, filed May 1, 2001, entitled "Method For Immobilizing Oligonucleotides Employing the Cycloaddition Bioconjugation Method," have also demonstrated the derivatization of solid phases carrying primary amino groups with cross-linking agents, such as compounds having structures represented by general formula (12), which carry an amino specific group for the attachment to the solid phase, e.g. a hydroxysuccinimide group, and in addition either a diene or a dienophile group to enable a Diels-Alder reaction. Derivatized solid phases prepared by these methods are also suitable trapping agents according to the method of this invention.

Example 3 illustrates the principle of separating capped and uncapped oligonucleotides with a trapping agent. Briefly, a defined mixture of a 5'-terminal unprotected oligonucleotide and a contaminant oligonucleotide carrying a 5'-cyclohexadienyl moiety are incubated in a buffered solution with trapping agent (13) described in Example 1, which is derivatized with maleimide moieties. After a reaction time of 90 minutes at 70° C. the trapping agent is removed by centrifugation. The analysis of the supernatant reveals almost complete recovery of the unprotected oligonucleotide with only traces of the contaminant oligonucleotide.

As noted above, in a preferred embodiment of the present invention the cycloaddition reaction utilized to trap contaminant oligonucleotides is a Diels-Alder reaction. Thus, in one embodiment of the present invention the type B functional group is a diene and the type C functional group is a dienophile. In another embodiment, the type B functional group is a dienophile and the type C functional group is a diene.

The diene moiety, either as a type B functional group of the capping reagent or as a type C functional group of the trapping agent, is selected from the group of compounds including, but not limited to compounds having structures represented by formulas (16) to (22), or can potentially be any other diene that is capable of undergoing a Diels-Alder reaction.

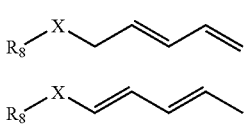

-continued

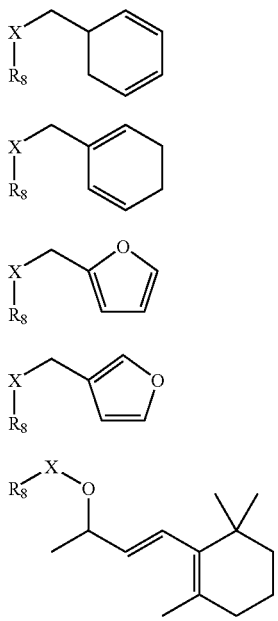

wherein $R_8$ represents either the solid phase of a trapping reagent, including the chemical moiety W generated during the derivatization of the solid phase as defined for formula (9) above or a type A functional group of a capping reagent as defined above;

X is an optional spacer unit selected from the group consisting of alkylenyl, diacyl, oligoethylene glycol, any combinations thereof, or any other chemical moiety known in the art that is suitable as part of a trapping agent to link a moiety $R_6$ to a solid phase or, as part of a capping reagent, to link functional groups without interfering with the processes involved in the oligonucleotide synthesis and purification as described herein.

An example of a diene derivatized capping reagent useful with the present invention is compound (23), described by Hill et al. (2001) J. Org. Chem. 66:5352–5358, which can be reacted with the hydroxyl groups of growing oligonucleotide chains in acetonitrile solution in the presence of an activator, e.g. 4,5-dicyanoimidazole.

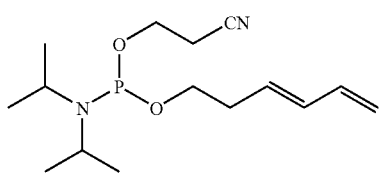

Another diene derivatized phosphoramidite suitable for use as a capping agent according to the method of this invention is compound (28), which was synthesized using the method described in Example 4. Briefly, with reference to Scheme 3 below, cyclohexadienylmethanol (24) prepared from cyclohexenylmethanol in three steps as described by Hill et al. (2001) J. Org. Chem. 66:5352–5358, which is incorporated herein by reference in its entirety, was reacted with aminohexanol (25) to provide the diene modified alcohol (26).

Compound (26) was then converted by reaction with 2-cyanoethyldiisopropylchlorophosphoramidite (27) into the diene phosphoramidite (28).

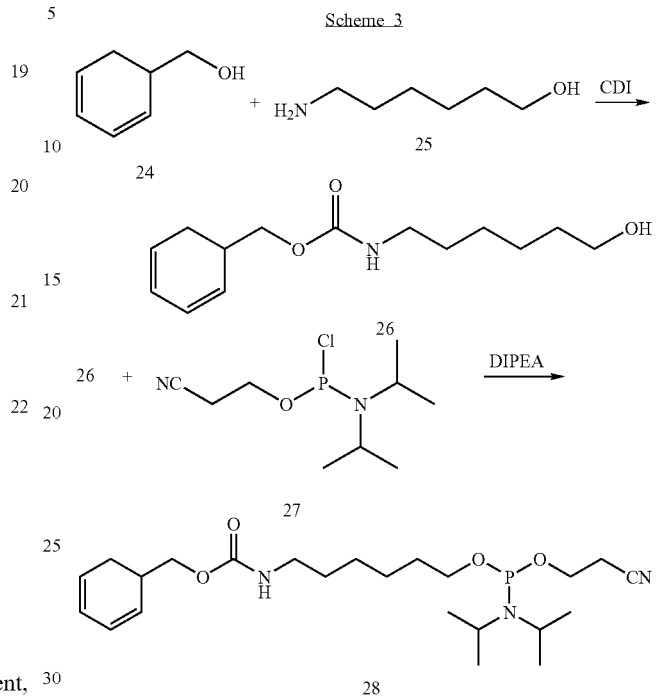

The dienophile moiety, either as a type B functional group of the capping reagent or as a type C functional group of the trapping agent is selected from the group of compounds including, but not limited to compounds having structures represented by formulas (29), (30) and (31), or can potentially be any other dienophile that is capable of undergoing a Diels-Alder reaction.

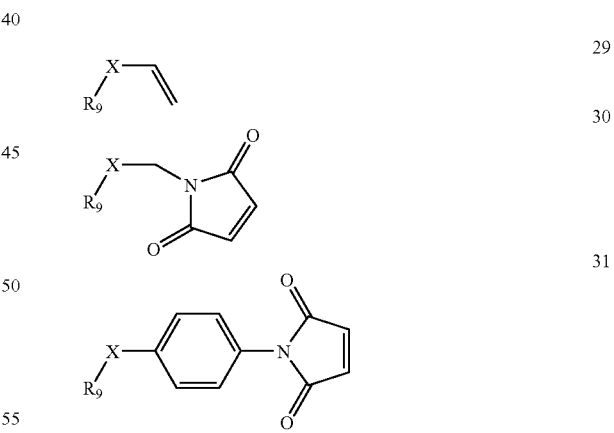

wherein $R_9$ represents either the solid phase of a trapping reagent, including the chemical moiety W generated during the derivatization of the solid phase as defined for formula (9) above or a type A functional group of a capping reagent as defined above;

X is an optional spacer unit selected from alkylenyl, diacyl, oligoethylene glycol, any combinations thereof, or any other chemical moiety known in the art that is suitable as part of a trapping agent to link a moiety $R_6$ to a solid phase or, as part of a capping reagent, to link functional groups without interfering with the processes involved in the oligonucleotide synthesis and purification as described herein.

Diels-Alder reactions, as described herein, are further characterized by yielding a cyclohexene derivative that serves as linking element immobilizing the contaminant oligonucleotides to the trapping agent.

The method for the integrated synthesis and purification of oligonucleotides is demonstrated in Examples 5 and 6, respectively. Example 5 describes the efficient capping of truncated sequences with the diene derivatized phosphoramidite (28) during the automated solid phase synthesis of an oligodeoxynucleotide, which is outlined in Scheme 4, below. As a model sequence d(TTTTTTTTTT)=dT$_{10}$ (SEQ ID NO:1) (32) was chosen. In order to demonstrate the process of removing diene capped truncated sequences via Diels-Alder conjugation (trapping), the ratio of truncated sequences was deliberately increased by decreasing the coupling efficiency of deoxythymidine phosphoramidite (33) employed in the synthesis of the model sequence (32). This was accomplished by decreasing the concentration of the dT phosphoramidite (33) from 0.1 M to 0.025M. The synthesis protocol was also modified to enable the use of diene derivatized phosphoramidite (28) as capping agent. Thus, instead of a single coupling step with the dT phosphoramidite (33) a sequence of two coupling steps was installed. First, compound (33) was pulsed through the column for 96 seconds followed by the application of a 0.1 M solution of compound (28) in acetonitrile for another 96 seconds. The original capping steps were not removed, but the Cap A and Cap B solutions were substituted with dry acetonitrile.

Figure 1:
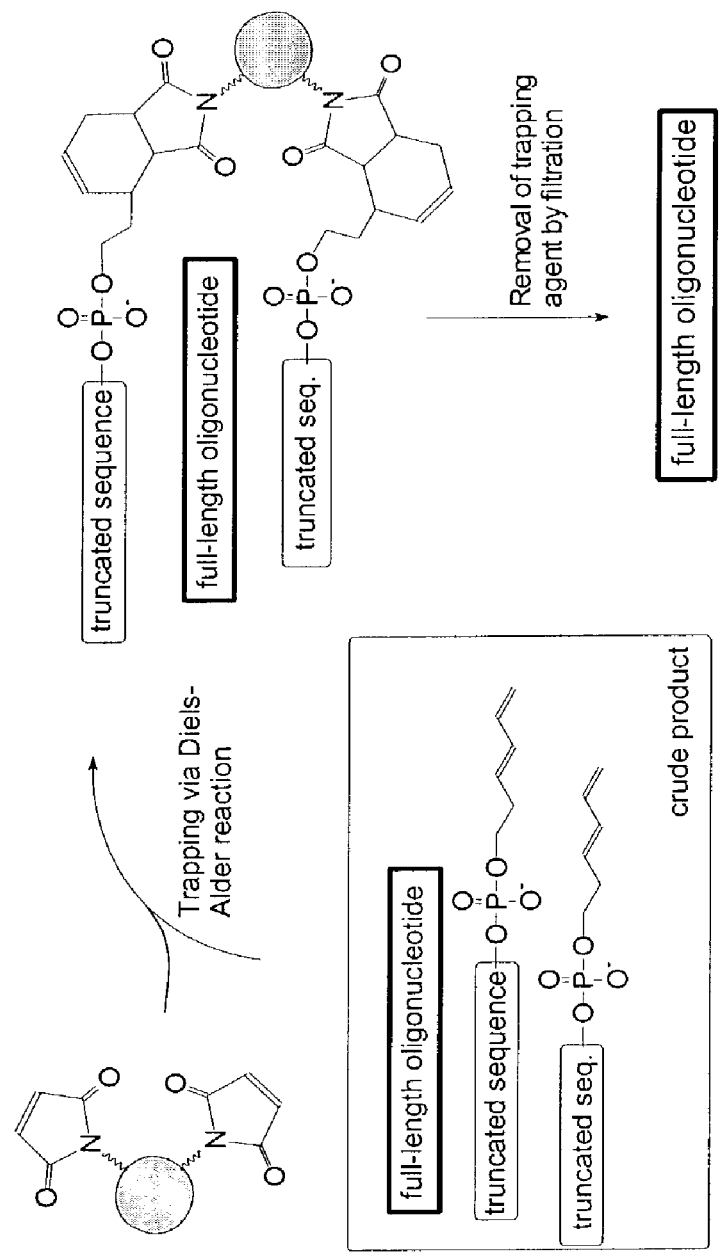
FIG. 1 illustrates the general principle of the trapping process of this invention, exemplified by the conjugation of a cap functionalized with a diene and a dienophile derivatized solid phase mediated by a Diels-Alder reaction.
Figure 2:
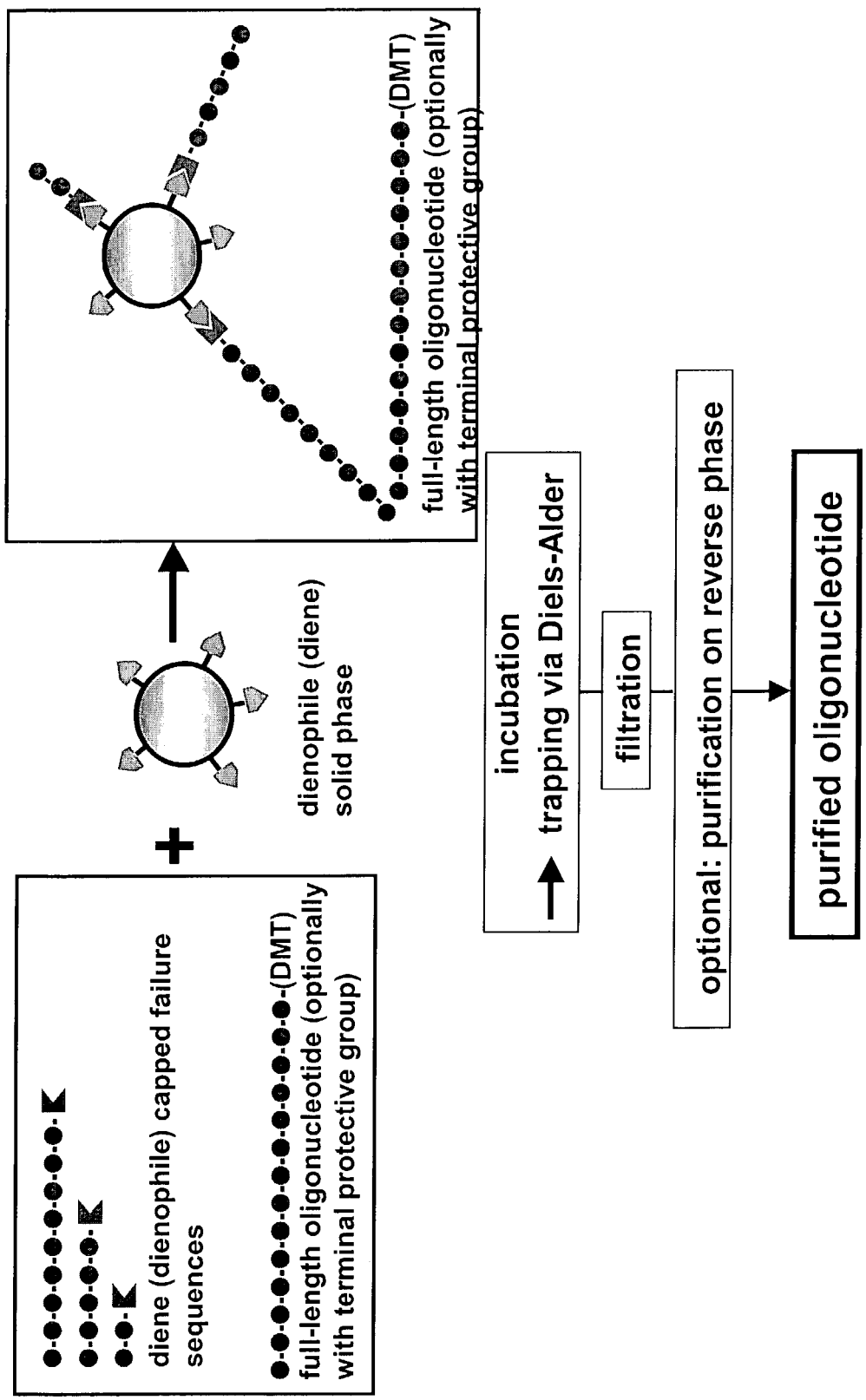
FIG. 2 is a schematic representation of a method of the invention for synthesizing and purifying an oligonucleotide employing trapping on solid phase based on a Diels-Alder reaction.
Figure 3:
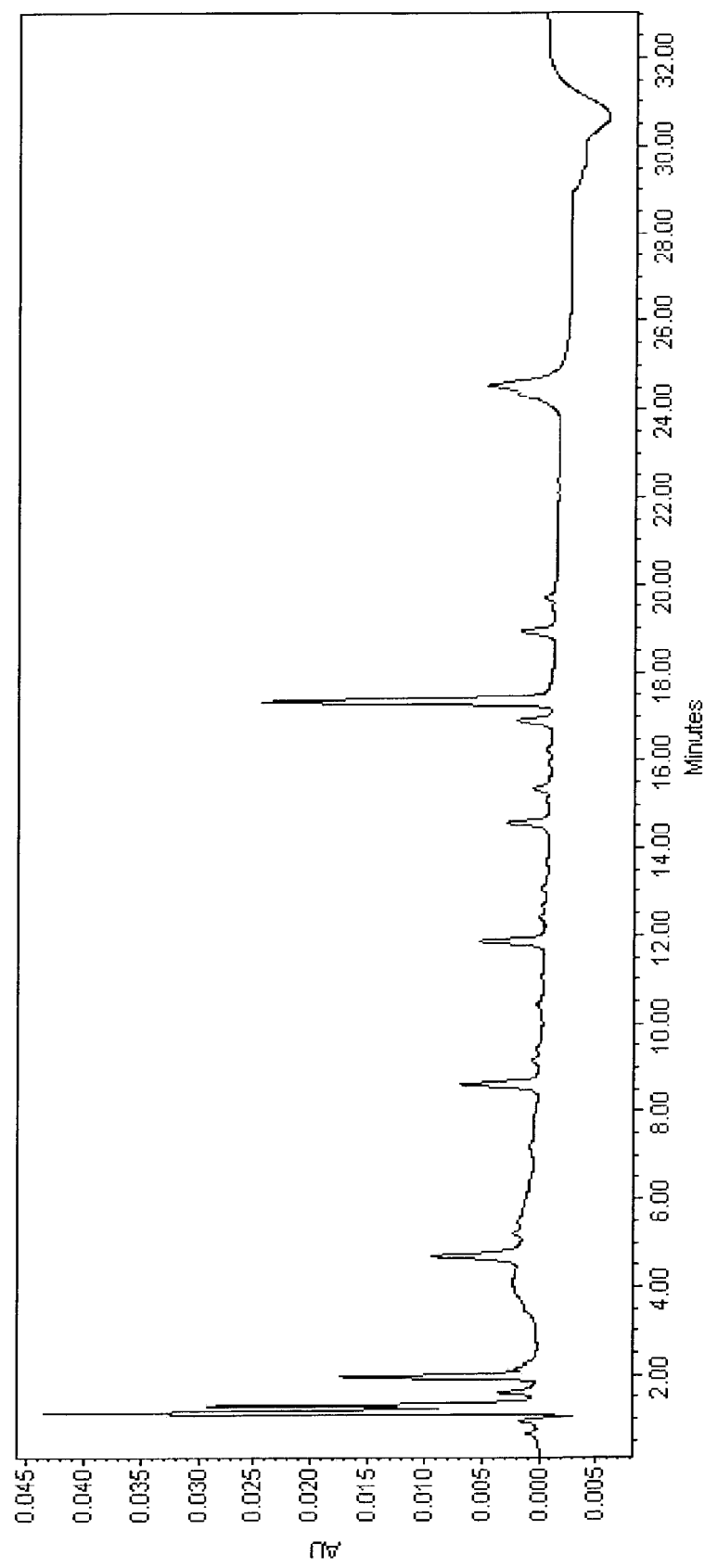
FIG. 3 shows the anion-exchange HPLC chromatogram of crude oligonucleotide (32) synthesized according to Example 5 applying a decreased concentration of phosphoramidite (33) in order to generate an increased level of failure sequences. Capping of failure sequences was performed with diene-modified phosphoramidite (28).

Following cleavage from the solid support and deprotection the purity of the synthesized oligonucleotide (32) was determined to be 39.1% by anion-exchange HPLC (FIG. 3). The generation of the desired full-length product (32) and the formation of diene tagged truncated sequences was confirmed by MALDI-MS (FIG. 4 and Table 1).

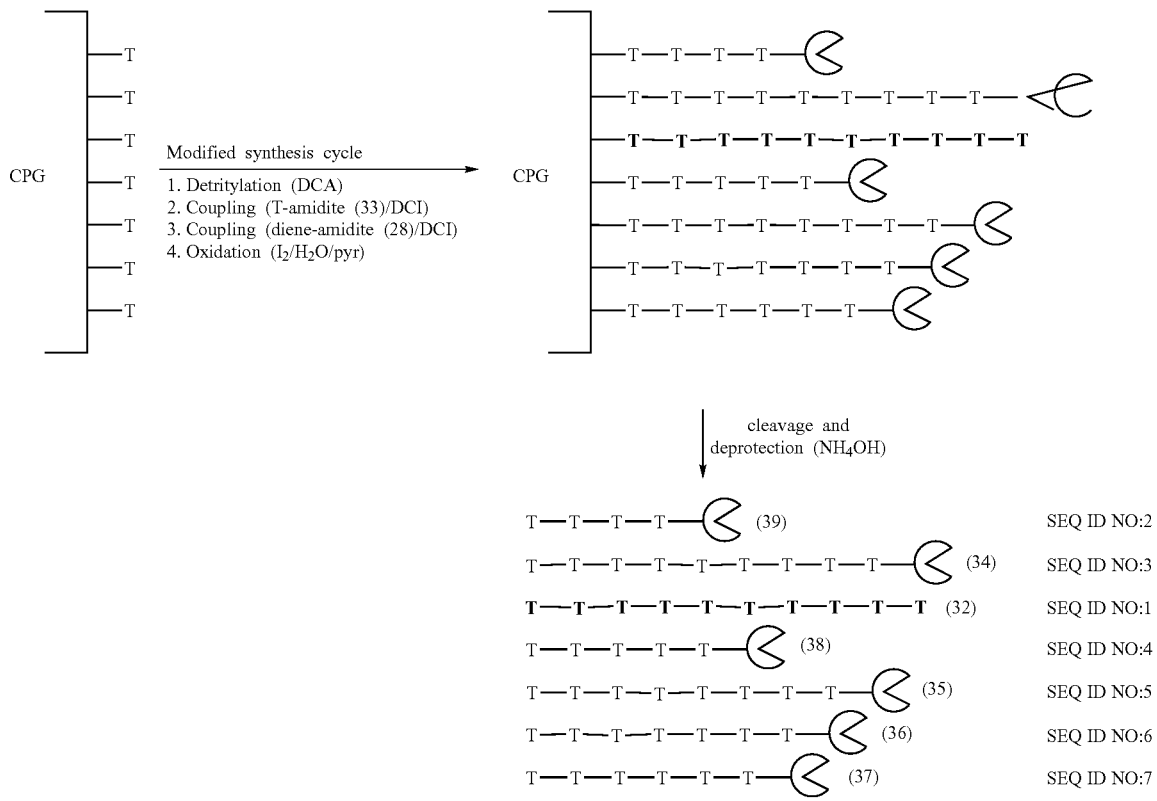

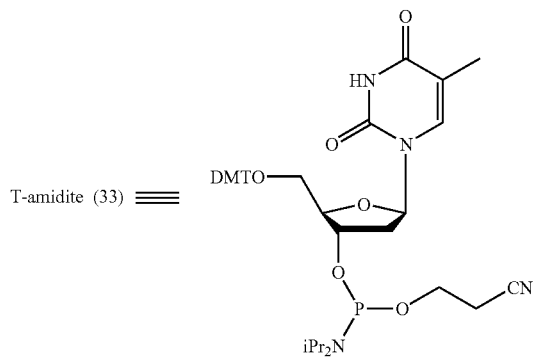

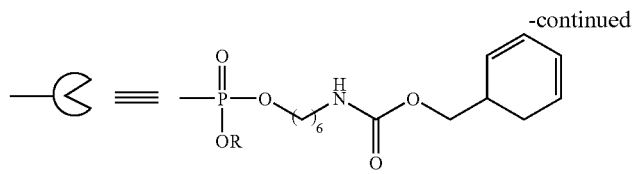

R = cyanoethyl or NH₄

TABLE 1

MALDI-MS analysis of crude product obtained from the synthesis of $T_{10}$ (32)

| Oligonucleotide | n-mer | Mass calcd | Found |
|---|---|---|---|
| 32 | 10 | 2980.0 | 2990.0 |
| 34 | 9 | 2991.1 | 2990.0* |
| 35 | 8 | 2686.9 | 2695.8 |
| 36 | 7 | 2381.7 | 2391.0 |
| 37 | 6 | 2078.5 | 2080.6 |
| 38 | 5 | 1774.3 | 1775.3 |
| 39 | 4 | 1470.1 | 1469.9 |

*the signal of compound (34) was overlaid by the signal of compound (32)

The removal of diene capped truncated sequences (34) to (39) by Diels-Alder conjugation to maleimide derivatized supports is described in Example 6 and illustrated in Scheme 5, below. For purification two aliquots of the crude oligonucleotide mixture from Example 5 were dissolved in phosphate buffer, pH 5.5. One sample was treated with the maleimide derivatized CPG (40) that was prepared with compound (14) according to Example 2. The second sample was treated with commercially available maleimide silica gel (41). Both samples were heated at 55° C for 1 hour. After separation of the insoluble support the solution was analyzed by anion-exchange HPLC (FIGS. 5 and 6) and MALDI-MS to confirm the improvement in the purity of full-length oligonucleotide (32), which was accomplished by removal of truncated sequences. The results obtained are summarized in Table 2.

TABLE 2

Analytical data of purified oligonucleotide (32)

| Sample | HPLC $R_t$ [min] | Purity [%] | MALDI-MS found (calcd: 2981.0) |
|---|---|---|---|
| Crude oligonucleotide (Example 5) | 17.34 | 39.1 | 2990.0 |
| Treated w/maleimide-CPG | 16.35 | 62.1 | 2985.2 |
| Treated w/maleimide silica gel | 16.36 | 70.9 | 2983.1 |

Scheme 5

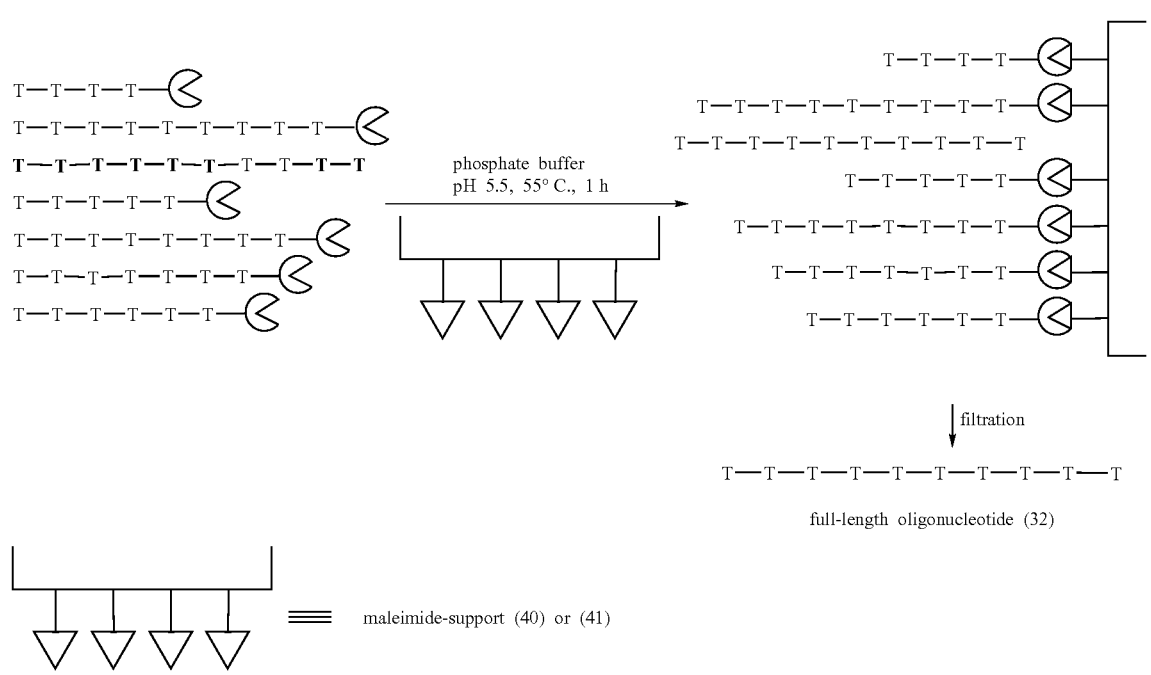

If the terminal protective group has been removed during step 1 of the above outlined method for the integrated synthesis and purification of oligonucleotides, the oligonucleotide product can be used as such or can be subjected to further work-up steps, e.g. desalting and/or concentration under reduced pressure, as described for example in Fischer et al. (1990) BioTechniques 9:300–301 and the Pharmacia Biotech NAP™-25 Column Instructions, both of which are incorporated herein by reference in their entirety.

If, on the other hand, the terminal protective group, commonly a dimethoxytrityl-group, has been retained in the last synthetic cycle performed in step 1, it can be utilized as a handle in an additional purification step on a hydrophobic stationary phase, e.g. by passing trough a reverse phase cartridge. In this case, the terminal protective group needs to be removed during or after the additional purification step, as described for example in Johnson et al. (1990) BioTechniques 8:424–428 and McBride and Caruthers (1988) BioTechniques 6:362–367, each of which is incorporated herein by reference in its entirety.

The following examples are provided for illustrative purposes only and are not intended to limit the scope of the invention.

EXAMPLES

Example 1

Derivatization of CPG with Maleimide-silane Reagent (10)

The maleimide functionality is introduced onto the CPG by condensation of hydroxy groups on the glass surface with the maleimide-silane reagent (10), which is synthesized as described by Pieken et al., U.S. patent application Ser. No. 09/845,742, filed May 1, 2001, entitled "Method For Immobilizing Oligonucleotides Employing the Cycloaddition Bioconjugation Method." Native CPG 500 (0.75 g) was shaken in a 10 vol-% solution of the maleimide-silane reagent (10) in toluene (2.6 mL) for 46 hours. The CPG was then collected on a glass-fritted funnel and washed sequentially with toluene (4×5 mL), methanol (8×4 mL) and methanol/water (1:1, v/v) (5 mL). The CPG was then transferred to a vial and shaken in methanol/water (1:1, v/v) (5 mL) for 0.5 hour. The CPG was again collected on a glass-fritted funnel and washed sequentially with methanol (4×4 mL) and ethyl acetate (3×4 mL). The powder was allowed to air dry in the funnel under suction for 2 minutes, transferred to a clean vial, placed in a vacuum desiccator, and dried in vacuo overnight. The light tan powder (0.6 g) was stored at −20° C. The maleimide loading of the CPG produced was determined by a modified Ellman's assay to be 159 µmol/g.

Example 2

Derivatization of CPG with Maleimide-silane Reagent (14)

The maleimide functionality is introduced onto the CPG by condensation of hydroxy groups on the glass surface with the maleimide-silane reagent (14), which is synthesized as described by Gunther et al. European Patent No. 0,982,311 A2. Native CPG 500 (2.5 g) was shaken in a 10 vol-% solution of the maleimide-silane reagent (14) in toluene (8.5 mL) for 43 hours. The CPG was then collected on a glass-fritted funnel using toluene (8 mL) and washed sequentially with toluene (4×8 mL), methanol (8×6 mL) and methanol/water (1:1, v/v) (10 mL). The CPG was then transferred to a vial and shaken in methanol/water (1:1, v/v) (10 mL) for 0.5 hour. The CPG was again collected on a glass-fritted funnel, this time using methanol (8 mL), and washed sequentially with methanol (4×8 mL) and ethyl acetate (3×10 mL). The powder was allowed to air dry in the funnel under suction for 2 minutes, transferred to a crystallization dish, placed in a vacuum desiccator, and dried in vacuo overnight. The white powder (2.5 g) was stored at −20° C. A sample was analyzed by a modified Ellman's assay and found to have a maleimide loading of 109 µmol/g.

Example 3

Removal of Diene-modified Oligonucleotide (42) from a Solution Containing a 5'-unprotected Oligonucleotide Via Maleimide-derivatized CPG

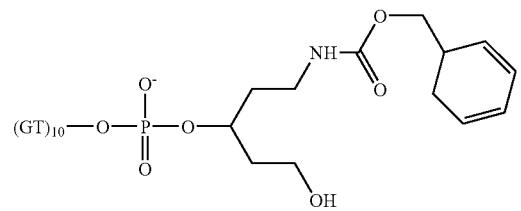

42

A mixture of the 5'-terminal diene-modified oligonucleotide $(GT)_{10}$, compound (42) (41.9 µg, 6.4 nmol), which was synthesized using the method of Hill et al. (2001) J. Org. Chem. 66:5352–58, and the unmodified oligonucleotide $(GT)_5$ (80.4 µg, 25 nmol) was prepared in 100 mM $Na_2HPO_4$ buffer at pH=5.5 (1 mL). An aliquot (100 µL) of the solution was removed for AX-HPLC analysis at the initial time point. CPG-maleimide (5 mg, 124 equivalents of maleimide to diene), prepared as described in Example 1 above, was added as a trapping agent to the oligonucleotide mixture, and the reaction was heated to 70° C. in a water bath for 90 minutes. At this time, subsequent to centrifugation an aliquot (100 µL) of the supernatant was removed and analyzed by AX-HPLC. On comparing the results of the HPLC analysis for the initial time point and the 90-minute time point it was determined that approximately 90% of the 5'-diene-oligonucleotide (42) was removed selectively by the trapping agent from the mixture of the diene modified oligonucleotide and the unmodified oligonucleotide.

Example 4

Synthesis of the Diene Derivatized Phosphoramidite (28)

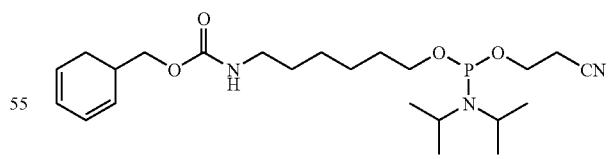

28

The synthesis of diene derivatized phosphoramidite (28) is outlined in Scheme 3. above.

a) Synthesis of Diene Modified Alcohol (26)

The alcohol (24) (3.09 g, 28.1 mmol), which was synthesized according to Hill et al. (2001) J. Org. Chem. 66:5352–5358, was dissolved in DMF (25 mL) and treated with 1,1'-carbonyldiimidazole (4.77 g, 29.4 mmol). The reaction mixture was purged with argon and stirred for 1 hour at room temperature. TLC analysis (hexanes/EtOAc 1:2) confirmed complete conversion of starting material. 6-Amino-1-hexanol (25) (3.00 g, 25.6 mmol) was added and stirring was continued overnight. The completion of the reaction was confirmed by TLC analysis (hexanes/EtOAc 1:2). The reaction mixture was concentrated and the residue dissolved in $CH_2Cl_2$ (50 mL) and extracted with water (30 mL). After separation, the organic layer was dried over $MgSO_4$, filtered, and concentrated. The crude product was recrystallized from dichloromethane to provide compound (26) (3.30 g, 46%) as white crystals. $R_f$ 0.56 (hexanes/EtOAc 1:2). mp 65° C. $^1H$ NMR (300 MHz, $CD_3CN$) δ 6.01–5.96 (m, 1H), 5.94–5.89 (m, 1H), 5.86–5.78 (m, 1H), 5.72–5.67 (m, 1H), 5.51 (sb, 1H), 3.96–3.89 (m, 2H), 3.49 (q, J=5.6 Hz, 2H), 3.08 (q, J=6.6 Hz, 2H), 2.68–2.50 (m, 1H), 2.49 (t, J=5.6 Hz, 1H), 2.31–2.21 (m, 1H), 2.15–2.02 (m, 1H), 1.54–1.45 (m, 4H), 1.40–1.26 (m, 4H). $^{13}C$ NMR (75 MHz, $CD_3CN$) δ 156.8, 127.0, 126.0, 125.6, 125.0, 61.7, 61.5, 40.7, 33.0, 32.8, 29.9, 26.5, 25.5, 25.0. MS (FAB) m/z 254 $[M+H]^+$.

b) Synthesis of (28)

To a solution of compound (26) (2.50 g, 9.9 mmol) and N,N-diisopropylethylamine (2.6 mL, 14.9 mmol) in THF (30 mL) was added under argon 2-cyanoethyldiisopropylchlorophosphoramidite (27, 2.34 g, 9.9 mmol). The mixture was stirred at room temperature until TLC analysis (EtOAc) indicated complete conversion of the starting material, approximately 1 hour. After concentration the residue was dissolved in $CH_2Cl_2$ (75 mL) and washed with saturated $NaHCO_3$ solution (2×75 mL) and brine (2×75 mL). After separation the organic layer was dried over $MgSO_4$, filtered, and concentrated. Purification by flash chromatography (20–100% EtOAc in hexanes, gradient elution) provided compound (28) (3.40 g, 76 %) as colorless oil. $R_f$ 0.83 (EtOAc). $^1H$ NMR (300 MHz, $CD_3CN$) δ 6.01–5.87 (m, 2H), 5.83–5.77 (m, 1H), 5.71 (m, 1H), 5.52 (bs, 1H), 3.97–3.89 (m, 2H), 3.89–3.70 (m, 2H), 3.70–3.56 (m, 4H), 3.07 (q, J=6.6 Hz, 2H),2.70–2.53 (m, 1 H), 2.66 (t, J=5.9 Hz, 2H), 2.31–2,15 (m, 1H), 2.15–2.01 (m, 1H), 1.64–1.26 (m, 8H), 1.20 (s, 3H), 1.19, (s, 3H), 1.18 (s, 3H), 1.17 (s, 3H). $^{13}C$ NMR (75 MHz, $CD_3CN$) δ 156.7, 127.0, 125.8, 125.3, 124.0, 118.9, 65.7, 63.6, 63.4, 58.6, 58.4, 43.1, 42.9, 40.7, 33.2, 31.2, 31.1, 29.9, 26.3, 25.6, 25.0, 24.2, 24.1, 20.4, 20.3. $^{31}P$ NMR (121 MHz, $CD_3CN$) δ 148.0. MS (FAB) m/z 455 $[M+H]^+$. Anal. Calcd. for $C_{23}H_{40}N_3O_4P$: C, 60.91; H, 8.89; N, 9.26. Found: C, 60.55; H, 9.23; N, 9.10.

Example 5

Automated Solid Phase Synthesis of a $T_{10}$ Oligodeoxynucleotide Employing Diene Derivatized Phosphoramidite (28) as Capping Agent Oligonucleotide (28) was synthesized on functionalized controlled pore glass (CPG) using an ABI Expedite (Model 8909) DNA synthesizer. In addition to the standard reagents for detritylation (deblocking) and oxidation the following reagents were used: a 0.025 M solution of dT phosphoramidite (33) in dry acetonitrile for coupling and a 0.25 M solution of 4,5-dicyanoimidazole (DCI) in dry acetonitrile as an activator. For capping, a 0.1 M solution of compound (28) in dry acetonitrile was employed. Cap A and Cap B solutions were replaced with dry acetonitrile. A modified synthesis protocol was created to incorporate capping with compound (28). Within the coupling step, the phosphoramidites (33) and (28) were delivered in sequence, each time applying the standard coupling time. All other steps in the protocol supplied by the manufacturer were used without modification, as set forth in Table 3. The synthesis was performed in DMT-Off mode including a final detritylation. The oligonucleotide was cleaved from the CPG support by treatment with 30% $NH_4OH$ for 45 minutes at ambient temperature. The supernatant was then removed from the CPG and incubated at 55° C. for 8 hours for deprotection. The crude oligonucleotide solution was evaporated to dryness in a SpeedVac and reconstituted in water (1 mL). Characterization of the product was performed by MALDI-MS (Table 1) and the purity determined by anion-exchange HPLC analysis on a DNAPac PA100 (13 μm; 0.1 μm; 4.0 mm×250 mm) eluting with a linear gradient from 10% to 46% B in 22.00 minutes at a flow rate of 1.5 mL $min^{-1}$. Detection was performed on a photodiode array detector with quantitation performed at λ=260 nm. 25 mM Trizma hydrochloride/1 mM EDTA/10% $CH_3CN$ was used as Buffer A and 25 mM Trizma hydrochloride/1 mM EDTA/10% $CH_3CN$/1 M NaCl was used as Buffer B. The purity of the full-length oligonucleotide (32) was determined as 39.1% ($R_t$=17.33 min.).

TABLE 3

Modified Expedite synthesizer protocol used in Example 5

Modified Synthesis Cycle

Deblocking

| Code | Deblocking Step | # of pulses | Volume (μL) | Time (s) |
|---|---|---|---|---|
| 144 | Index Fract. Column | NA | 16 | 0 |
| 0 | Default | Wait | 0 | 1.5 |
| 141 | Trityl Monitor On/Off | NA | 1 | 1 |
| 16 | Deblock | 10 | 160 | 0 |
| 16 | Deblock | 50 | 800 | 49 |
| 38 | Diverted ACN Wash | 40 | 640 | 0 |
| 141 | Trityl Monitor On/Off | NA | 0 | 1 |
| 38 | Diverted ACN Wash | 40 | 640 | 0 |
| 144 | Index Fract. Column | NA | 16 | 0 |

Coupling

| Code | Coupling Step | # of pulses | Volume (μL) | Time (s) |
|---|---|---|---|---|
| 1 | ACN Wash | 5 | 80 | 0 |
| 2 | Activator (DCI) | 5 | 80 | 0 |
| 21 | Amidite (33) + Activator | 6 | 96 | 0 |
| 21 | Amidite (33) + Activator | 1 | 16 | 8 |
| 2 | Activator (DCI) | 4 | 64 | 32 |
| 2 | Activator (DCI) | 7 | 112 | 56 |
| 2 | Activator (DCI) | 8 | 128 | 0 |
| 24 | Amidite (28) + Activator | 6 | 96 | 0 |
| 24 | Amidite (28) + Activator | 1 | 16 | 8 |
| 2 | Activator (DCI) | 4 | 64 | 32 |
| 1 | ACN Wash | 7 | 112 | 56 |
| 1 | ACN Wash | 8 | 128 | 0 |

Capping

| 12 | ACN Wash | 20 | 320 | 0 |
| 13 | Cap A & B | 8/each | 128×2= 256 | 0 |
| 12 | ACN Wash | 6 | 96 | 15 |
| 12 | ACN Wash | 14 | 224 | 0 |

Oxidizing

| 15 | Oxidizer | 15 | 240 | 0 |
| 12 | ACN Wash | 15 | 240 | 0 |

Capping

| 13 | Cap A & B | 7/each | 112 × 2 = 224 | 0 |
| 12 | ACN Wash | 30 | 480 | 0 |

Abbreviations: ACN = acetonitrile; DCI = 4,5-dicyanomidizole.

Example 6

Removal of Diene-capped Truncated Sequences by Diels-Alder Conjugation to Maleimide-supports The crude product from Example 5 was dissolved in 1 mL of water and assayed for total oligonucleotide content via $OD_{260}$ analysis to be 14.7 OD/mL. Two aliquots of 250 μL (3.7 OD), each, were removed from this solution and evaporated to dryness. The samples were resuspended in 1.0 mL, each, of 250 mM sodium phosphate/biphosphate buffer ($Na_2HPO_4/NaH_2PO_4$, pH 5.5) with shaking at room temperature for 90 minutes. Two maleimide supports were used to determine the effectiveness of removing the diene capped failure sequences from the crude oligonucleotide solution: the maleimide-CPG synthesized according to Example 2, referred to for ease of reference as compound (40), with a loading of 100 μmol/g and a commercial maleimide functionalized silica gel, referred to for ease of reference as compound (41) (from Silicycle, Quebec, Canada. Cat.#R71030B) with a loading of 740 μmol/g. The maleimide reagents were added to the respective vials, and the vials were capped and vortexed to ensure good mixing and exposure of the reagent to the oligo solution. The vials were then heated under shaking at 55° C. for 1 hour. Each sample was evaporated to dryness using a SpeedVac and resuspended in 150 μL, each, of water. Each sample (75 μL) was then transferred to another vial and diluted with water (75 μL) for HPLC analysis. The samples were analyzed using the anion-exchange HPLC method described in Example 5 (FIGS. 5 and 6). Characterization of oligonucleotide (32) was performed by MALDI-MS. The analytical results are provided in Table 2.

---

The invention claimed is:

1. A method for the synthesis and purification of oligonucleotides comprising the steps of:
   (a) synthesizing an oligonucleotide pursuant to standard techniques for solid phase oligonucleotide synthesis (SPOS), wherein during the capping step of each synthetic cycle a cap derivatized with a moiety capable of undergoing a cycloaddition reaction is introduced to unreacted terminal functional groups of the growing oligonucleotide chain which failed to be elongated in the preceding coupling step, wherein the corresponding capping agent comprises functional groups A and B, functional group A being reactive to terminal functional groups of the oligonucleotide and functional group B being able to participate in a cycloaddition reaction;
   (b) cleaving the oligonucleotide from the solid phase synthesis support, and, either deprotecting the oligonucleotide compound completely, or deprotecting the oligonucleotide compound completely except for the terminal protective group;
   (c) adding a trapping agent to the product obtained following step (b), wherein said trapping agent is comprised of a solid phase derivatized with functional groups C, wherein the functional groups C are capable of undergoing a cycloaddition reaction with the functional groups B that were part of the capping agent in step (a), and incubating the resulting mixture under conditions of time and temperature that promote a cycloaddition reaction between the functional groups B and C, and
   (d) separating the trapping agent from the remainder of the reaction mixture.

2. The method of claim 1, wherein said oligonucleotide is a single stranded chain selected from the group consisting of deoxyribonucleotides, ribonucleotides and chemical modifications thereof.

3. The method of claim 1, wherein said solid phase is selected from the group consisting of silica, alumina, zeolites, controlled pore glass, polystyrene, polyacrylamide, polymethacrylate, polyvinylalcohol, polyethylene glycol and derivatives thereof, other synthetic polymers, polymeric carbohydrates, other organic polymers and any copolymers, composite materials and combination of the above inorganic or organic materials.

4. The method of claim 1, wherein the terminal protective group of the fully elongated oligonucleotide is not removed, allowing for an additional purification step by separating the terminal protected oligonucleotide compound from contaminants on an appropriate stationary phase.

5. The method of claim 4, wherein said terminal protective group is a dimethoxytrityl group and the stationary phase is of hydrophobic material.

6. The method of claim 1, wherein said synthesis of the oligonucleotide compound is performed in a 3' to 5' direction by coupling a nucleotide monomer carrying a protective group at the 5'-position and an activating group at the 3'-position intended to build up a linkage to the 5'-terminus of the growing chain.

7. The method of claim 1, wherein said synthesis of the oligonucleotide compound is performed in a 5' to 3' direction by coupling a nucleotide monomer carrying a protective group at the 3'-position and an activating group at the 5'-position intended to build up a linkage to the 5'-terminus of the growing chain.

8. The method of claim 1, wherein said cycloaddition reaction is a Diels-Alder reaction.

9. The method of claim 1, wherein said functional group B is a diene and the functional group C is a dienophile.

10. The method of claim 1, wherein said functional group B is a dienophile and the functional group C is a diene.

11. The method of claim 1, wherein said unreacted terminal functional group is a hydroxy group.

12. The method of claim 11, wherein said capping reagent is selected from a compound having the following structural formula:

$$R_1—X—R_2$$

wherein
- $R_1$ is functional group A;
- $R_2$ is functional group B; and
- X is an optional spacer unit selected from the group consisting of alkylenyl, diacyl, oligoethylene glycol, or any combinations thereof;

wherein said functional group A is a moiety selected from the group consisting of formula (II), (III) and (IV)

$$—N=C=O \quad \quad (II)$$

$$—O—P(=O)(—H)(—O^-Y^+) \quad \quad (III)$$

$$—O—P(—R_4(—O—R_3)) \quad \quad (IV)$$

wherein
- $R_3$ is a protective group selected from the group comprising 2-cyano-ethyl, methyl or allyl;
- $R_4$ is dialkylamino with alkyl having from one to about six carbons, or a cyclic substituent attached via a nitrogen atom that is part of the ring system, the ring system containing from 4 to 7 carbons and up to 3 heteroatoms; and
- Y is selected from the group comprising ammonium, lower alkylammonium, pyridinium, lutidinium and metal salt cations.

13. The method of claim 12, wherein said functional group B is a conjugated diene selected from the group consisting of alkyldienes, cyclohexadienes, furans, beta-Ionol, and derivatives thereof.

14. The method of claim 12, wherein said functional group B is a dienophile selected from the group consisting of an alkene, maleimide, and derivatives thereof.

15. The method of claim 1, wherein said trapping agent is selected from the group of compounds having structural formula (V):

$$R_5—W—X—R_6 \quad \quad V$$

wherein
- $R_5$ represents the solid phase;
- $R_6$ is functional group C;
- X is an optional spacer unit selected from the group consisting of alkylenyl, diacyl, oligoethylene glycol, any combinations thereof; and
- W is the chemical moiety generated by said derivatization of the trapping agent originating from the functional group on the solid phase and is selected from the group consisting of O, NH, NH(CO)O, NH(CS)O, NH(CO)NH, NH(CO), (CO)NH and a moiety derived from introducing silyl groups selected from the group consisting of $O_3Si$ (three linkages to the solid phase), $O_2(R_7)Si$ (two linkages to the solid phase), $O(R_7)_2Si$ (one linkage to the solid phase), wherein $R_7$ is selected from an alkyl with a carbon chain of up to 20 carbon atoms.

16. The method of claim 15, wherein said functional group C is a conjugated diene selected from the group consisting of alkyldienes, cyclohexadienes, furans, beta-Ionol, and derivatives thereof.

17. The method of claim 15, wherein said functional group C is a dienophile selected from the group consisting of an alkene, maleimide, and derivatives thereof.

18. A compound having the following formula $$R_1—X—R_2$$

wherein
- $R_1$ is —N=C=O;
- $R_2$ is a conjugated diene selected from the group consisting of cyclohexadienes, beta-Ionol, and derivatives thereof; and
- X is an optional spacer unit selected from the group consisting of alkylenyl, diacyl, oligoethylene glycol, any combinations thereof.

19. A compound having the following formula $$R_1—X—R_2$$

wherein
- $R_1$ —N=C=O;
- $R_2$ is a dienophile selected from the group consisting of an alkene maleimide, and derivatives thereof; and
- X is a spacer unit selected from the group consisting of alkylenyl, diacyl, oligoethylene glycol, any combinations thereof.

20. A compound having the following formula $$R_1—X—R_2$$

wherein
- $R_1$ is $—O—P(=O)(—H)(—O^-Y^+)$;
- $R_2$ is a conjugated diene selected from the group consisting of alkyldienes, cyclohexadienes, furans, beta-Ionol, and derivatives thereof;
- Y is selected from the group comprising ammonium, lower alkylammonium, pyridinium, lutidinium and metal salt cations; and
- X is an optional spacer unit selected from the group consisting of alkylenyl, diacyl, oligoethylene glycol, any combinations thereof.

21. A compound having the following formula $$R_1—X—R_2$$

wherein
- $R_1$ is $—O—P(=O)(—H)(—O^-Y^+)$;
- $R_2$ is a dienophile selected from the group consisting of an alkene, maleimide, and derivatives thereof;
- Y is selected from the group comprising ammonium, lower alkylammonium, pyridinium, lutidinium and metal salt cations; and
- X is an optional spacer unit selected from the group consisting of alkylenyl, diacyl, oligoethylene glycol, any combinations thereof.

22. A compound having the following formula $$R_1—X—R_2$$

wherein
- $R_1$ is —N=C=O;
- $R_2$ is a conjugated diene selected from the group consisting of alkyldienes, furans and derivatives thereof; and
- X is a spacer unit selected from the group consisting of alkenyl, diacyl, oligoethylene glycol, any combinations thereof.

* * * * *